US005869057A

United States Patent [19]

Rock

[11] Patent Number: 5,869,057

[45] Date of Patent: Feb. 9, 1999

[54] RECOMBINANT VACCINES TO BREAK SELF-TOLERANCE

[76] Inventor: Edwin P. Rock, 4535 Hawthorne St., Washington, D.C. 20016

[21] Appl. No.: 944,982

[22] Filed: Oct. 7, 1997

Related U.S. Application Data

[63] Continuation of Ser. No. 472,455, Jun. 7, 1995, abandoned.

[51] Int. Cl.[6] ...................... A61K 39/108; C07K 14/245; C07H 21/02

[52] U.S. Cl. ..................... 424/192.1; 435/69.3; 530/403; 536/23.5; 536/23.7

[58] Field of Search ........................ 424/192.1; 435/69.3; 530/403; 536/23.5, 23.7

[56] References Cited

U.S. PATENT DOCUMENTS

| | | | |
|---|---|---|---|
| 4,201,770 | 5/1980 | Stevens | 427/177 |
| 4,384,995 | 5/1983 | Stevens | 260/112.5 R |
| 4,526,716 | 7/1985 | Stevens | 260/112.5 R |
| 4,691,006 | 9/1987 | Stevens | 530/324 |
| 4,713,366 | 12/1987 | Stevens | 514/13 |
| 4,762,913 | 8/1988 | Stevens | 530/345 |
| 4,767,842 | 8/1988 | Stevens | 530/324 |
| 4,855,285 | 8/1989 | Stevens | 514/12 |
| 5,006,334 | 4/1991 | Stevens | 424/88 |
| 5,241,053 | 8/1993 | Fujisawa et al. | 424/89 |
| 5,268,276 | 12/1993 | Holmgren et al. | 435/5 |
| 5,308,835 | 5/1994 | Clements | 514/12 |

OTHER PUBLICATIONS

Haynes et al. Bio/Technology vol. 4, Jul. 1986, pp. 637–641.

Clements et al. Immunopharmacology Inf Dis:Vaccine Adjuvants and Modulators of Non–Specific Resistance, pp. 139–154 1987.

Nardi et al. Molecular Medicine, vol. 1, No. 5, 1995, pp. 563–567.

Triozzi et al. Ann. New York Acad Sci, vol. 690, 1993, pp. 358–359.

Lipscombe et al. Mol Microbiol vol. 5 No. 6, 1991, pp. 1385–1392.

Gicquel, B. "Toward new . . . ". 1994. Recomb. Vect. in Vacc. Develop., pp. 171–178. Karger, New York.

Curtiss, R., et al. "Recombinant . . . ". 1994. Recomb. Vect. in Vacc. Develop., pp. 23–33. Karger, New York.

Lebens, M., et al. "Mucosal . . . " 1994. Recomb. Vect. in Vacc. Develop., pp. 215–227. Karger, New York.

Stover, C.K., et al. "Protective . . . ". 1994 Recomb. Vect. in Vacc. Develop., pp. 163–170. Karger, New York.

Barber, L.D., et al. "The essence . . . ". 1994. Jour. of Exp. Med. vol. 180, pp. 1191–1194.

Cardenas, L., et al. "Oral immunization . . . " 1992. Clinical Microbiology Rev. vol. 5, pp. 328–342.

Dale, J.B. and Chiang, E.C. "Intranasal . . . ". 1995. The Journal of Infect. Dis. vol. 171, pp. 1038–1041.

Gonzales, C., et al. "*Salmonella typhi* . . . ". 1994. Jour. Of Infect. Dis. vol. 169. pp. 927–931.

Holmgren, J., et al. "Cholera toxin and cholera B . . . ". 1993. Vaccine, vol. 11, pp. 1179–1184.

Lagranderie, M., et al. "Oral immunization with . . . ". 1993. Vaccine. vol. 11, pp. 1283–1290.

Langerman, S., et al. "Systemic and mucosal immunity . . . ". 1994. Nature. vol. 372, pp. 552–555.

Murray, A., et al. "Expression of *Escherichia coli* . . . ". 1992. Molec. Microbiol. vol. 6, pp. 3331–3342.

Nashar, T.O., et al. "Current progress in . . . ". 1993. Vaccine. vol. 11. pp. 235–240.

Pan, Z.–K., et al. "A recombinant Listeria . . . ". Nature Medicine. vol. 1, pp. 471–477.

Pardoll, D.M. "Cancer vaccines" 1993. Trends in Pharmaceutical Sciences. vol. 14. pp. 202–208.

Schodel, F., et al. "Hepatitis B virus core . . . ". 1994 Int. Rev. of Immunol. vol. 11. pp. 153–165.

Stover, C.K., et al. "New use of BCG for recombinant vaccines." 1991. Nature. vol. 456, pp. 456–460.

Sun, J.–B., et al. "Cholera toxin B . . . ". 1994. Proc. Ntnl. Acad. Sci. (USA) vol. 91, pp. 10795–10799.

Wucherpfenning, K.W., et al. "Selective binding . . . ". Journal of Exp. Med. vol. 181, pp. 1597–1601.

*Primary Examiner*—Ponnathapura Achutamurthy
*Assistant Examiner*—Phuong T. Bui
*Attorney, Agent, or Firm*—Keil & Weinkauf

[57] ABSTRACT

This invention relates to vaccines, specifically to the use of recombinant DNA technology to immunize against self proteins and to induce antibody against self protein in mammals. A process is described in which DNA sequences encoding a microbial gene product and a self gene protein are joined and expressed by means of a suitable DNA vector and a non-pathogenic microbial strain. The present invention further relates to the isolation and purification of a fusion peptide combining the non-toxic B subunit of an enterotoxigenic strain of *E. coli* (LTB) with the carboxyl terminal peptide (CTP) of human chorionic gonadotropin (hCG), as well as to the use of this fusion protein for immunological prophylaxis and therapy.

5 Claims, 12 Drawing Sheets

CTP-A: 5' terminus

```
        1              9              18              27              36
5'      GT CCC AAG GAC CAC CTG CAG ACC AGT GAT GAC CCC CGC TTC AGG   3'
             P   K   D   H   P   L   T  C->S D   D   P   R   F   Q
                                (PstI)
```

CTP-B: 3' terminus

```
        1              9              18              27
5'      CGG ATT GAG AAG CCT TTA TTG TTG GAG GAT CGG      3'
                            stop  Q   P   L   I   P
                      (HindIII)
```

FIG. 1

NUCLEOTIDE SEQUENCE OF LTB-CTP FUSION PROTEIN GENE IN PLASMID pRE201

```
                                 -21                  -15                  -10                  -5              -1
>
GAATTCGGAATGAATT ATG AAT AAA GTA AAA TGT TAT GTT TTA TTT ACG GCG TTA CTA TCC TCT CTA TGT GCA TAC GGA
 .  .  .  .  .   M   N   K   V   K   C   Y   V   L   F   T   A   L   L   S   S   L   C   A   Y   G

 1               5                  10                  15                  20                  25
GCT CCC CAG TCT ATT ACA GAA CTA TGT TCG GAA TAT CGC·AAC ACA CAA ATA TAT ACG ATA AAT GAC AAG ATA CTA
A   P   Q   S   I   T   E   L   C   S   E   Y   R   N   T   Q   I   Y   T   I   N   D   K   I   L

26               30                 35                  40                  45                  50
TCA TAT ACG GAA TCG ATG GCA GGC AAA AGA GAA ATG GTT ATC ATT ACA TTT AAG AGC GGC GCA ACA TTT CAG GTC
S   Y   T   E   S   M   A   G   K   R   E   M   V   I   I   T   F   K   S   G   A   T   F   Q   V
```

FIG. 4A

```
51                  55                       60                       65                       70                       75
GAA GTC CCG GGC AGT CAA CAT ATA GAC TCC CAA AAA AAA GCC ATT GAA AGG ATG AAG GAC ACA TTA AGA ATC ACA
E   V   P   G   S   Q   H   I   D   S   Q   K   K   A   I   E   R   M   K   D   T   L   R   I   T

76                  80                       85                       90                       95                      100
TAT CTG ACC GAG ACC AAA ATT GAT AAA TTA TGT GTA TGG AAT AAT AAA ACC CCC AAT TCA ATT GCG GCA ATC AGT
Y   L   T   E   T   K   I   D   K   L   C   V   W   N   N   K   T   P   N   S   I   A   A   I   S

           |    105                      110         |            115                      120                     125
ATG GAA AAC|CAT GAT CCC CGG GTA CCC GGG CTG CAG|ACC AGT GAT GAC CCC CGC TTC CAG GAC TCC TCT TCC TCA
M   E   N  |H   D   P   R   V   P   G   L   Q  |T   S   D   D   P   R   F   Q   D   S   S   S   S

126                 130                      135                      140                      145                 149
AAG GCC CCT CCC CCG AGC CTT CCA AGT CCA TCC CGA CTC CCG GGG CCC TCG GAC ACC CCG ATC CTC CCA CAATAAAGC
K   A   P   P   P   S   L   P   S   P   S   R   L   P   G   P   S   D   T   P   I   L   P   Q   .  .
```

FIG. 4B

RECOMBINANT VACCINES TO BREAK SELF-TOLERANCE

This application is a continuation of application Ser. No. 08/472.455, filed on Jun. 7, 1995, now abandoned.

1 INTRODUCTION

This invention relates to vaccines, specifically to the use of recombinant DNA technology to immunize humans against human (self) proteins. A process is described in which DNA sequences encoding a microbial gene product and a self gene protein are joined and expressed by means of a suitable DNA vector and a non-pathogenic microbial strain.

The present invention further relates to the isolation and purfication of a fusion peptide combining the non-toxic B subunit of an enterotoxigenic strain of *E. coli* (LTB) with the carboxyl terminal peptide (CTP) of human chorionic gonadotropin (hCG), as well as to the use of this fusion protein for immunological prophylaxis and therapy.

2 BACKGROUND AND PRIOR ART

2.1 The Problem of Self-Tolerance

2.1.1 The Nature of Specific Immunity: Self-Nonself Discrimination

Self-nonself discrimination refers to the process by which a mammal's immune system identifies and reacts specifically against "foreign" entities such as infectious disease agents, tumors, or tissue transplanted from a genetically nonidentical individual. This topic is reviewed at length in William Paul's book, Fundamental Immunology (3rd edition, 1993, Raven Press, New York). Specificity is engendered principally by B and T lymphocytes, which are similar morphologically and develop from common stem cell precursors. B cells express antibodies either as cell-surface receptors or as secreted molecules called antibodies (or immunoglobulins, Ig). Immunoglobulins bind to a virtually infinite array of antigenic surfaces. T cells, on the other hand, bear generally surface-bound T cell receptors which typically are specific for a composite of peptide antigen (generally nine or ten amino acids) bound to a transplantation antigen of the major histocompatibility complex (MHC, called HLA in humans). These two recognition systems are intimately linked by the requirement of most B cell responses (secreted Ig) for "T cell help" in the form of specific growth and differentiation factors known as lymphokines. T cells also act directly in the eradication of virally infected or malignantly transformed cells.

Inherent in the process of self-nonself discrimination is the concept of self-tolerance. Self-tolerance implies that an individual's immune system will not react to "self" molecules, i.e. those from that individual (or a genetically identical individual as in inbred mice). Self-tolerance is due primarily to the absence (via thymic selection) or inactivation (called anergy) of T cells with specificity for complexes of self-peptide with self-MHC.

T cell receptors are of two types, each of which is encoded by two distinct gene families: alpha and beta or gamma and delta. Alpha-beta T cells predominate in the blood and lymphoid organs such as lymph nodes and spleen. Gamma-delta T cells on the other hand are preponderant in epithelia including skin and mucosal surfaces of the gastrointestinal, respiratory, and urogenital tracts. While peptide-MHC complexes are clearly the primary target of alpha-beta TCR, the antigenic ligands recognized by gamma-delta TCR are likely to be different and might include non-peptide microbial antigens commonly encountered at epithelial boundaries.

Alpha-beta T cells mature in the thymus (hence the name "T" cell), where at least 99% of them die. This process is called thymic selection or thymic maturation. Those functional cells emerging from the thymus are both "positively" and "negatively" selected. Positive selection implies that they have weakly recognized "self" MHC molecules, i.e. those present in the thymus during initial alpha-beta T cell maturation. Negative selection indicates that mature T cells will not in general react to self MHC molecules without the presence of a foreign peptide, i.e. that developing T cell clones in the thymus which do strongly recognize complexes of a self-peptide with a self-MHC molecule are killed rather rather than allowed to exit the thymus. Thus self-tolerance occurs at least in part by virtue of clonal deletion of T cells specific for complexes of self-peptide with self-MHC.

Following thymic selection, an individual's T lymphocytes are endowed with the capacity to recognize "foreign" peptides in association with self-MHC and to initiate the cascade of reactions that constitues cell-mediated immunity. In contrast to recognition by immunoglobulins, which have long been known to exhibit broad affinities of interaction with a vast universe of antigens, peptide recognition by T cell receptors is of low affinity but exquisitely precise. That such interactions are the primary determinants of self-nonself discrimination is consistent with the amplification of response that can occur following specific, low affinity binding between a group of T cell receptors on one cell and a group of peptide-MHC complexes on another. This amplification entails intracellular signalling cascades and ultimately either lymphokine secretion or direct effector function by the stimulated T cell.

In order for stimulation of T cells to result in an activating response, costimulation must occur via contact between other cell surface receptors: B7 on the cell presenting peptide-MHC complexes, and either CD28 or CTLA-4 on the T cell. By contrast, if antigen-specific T cell receptors bind to a specific peptide-MHC complex in the absence of costimulation, specific nonresponsiveness or anergy results, and that particular T cell will no longer be capable of being activated. This process provides a second means by which T cells may be rendered specifically nonresponsive, i.e. self-tolerant.

Self-tolerance then is generated both by clonal deletion of autoreactive T cells during thymic selection and by clonal anergy. These processes are complementary in that the latter ensures that any potentially self-reactive T cells which have escaped thymic deletion subsequently lose their capacity to be activated by self protein fragments with self MHC. This loss of capacity to react is possibly due to an absence of costimulatory molecules as described above.

Most T cells in peripheral blood express one of two coreceptors, CD4 and CD8. $CD4^+$ T cells are more numerous and harbor specificity for peptides presented by class II MHC molecules (HLA DR, DP, DQ), which are found on the surface of specialized antigen presenting cells such as macrophages, dendritic cells, and B cells. Such cells typically present "exogenous" antigens that have been phagocytosed and degraded by the antigen presenting cell. $CD8^+$ cells on the other hand are specific for "engogenously" synthesized peptides that are bound in complexes with class I MHC molecules (HLA A, B, C). Class I molecules are present on all nucleated cells of the body. Most cytotoxic T lymphocytes (CTL) are $CD8^+$, and historically they are of greatest importance in antiviral immunity.

2.1.2 Vaccines and Infectious Diseases

Immunization describes the process of administering antigen to a live host with the purpose of inducing an immune response for either academic or public health reasons. Vaccination is the term for the second reason. Vaccines were developed primarily as a prophylactic measure to prevent disease caused by infectious agents. This topic has been reviewed at length by Gordon Ada in a chapter entitled "Vaccines" on pages 1309–1352 of the book entitled Fundamental Immunology (1993, edited by W. Paul. Raven Press, New York).

Effective vaccination is thought to depend on the generation of an immune response which possesses the properties of specificity and memory. Both specificity and memory are generated via division and differentiation of B and T lymphocytes which bear surface receptors specific for the antigen introduced.

Traditionally vaccines are suspensions of attenuated or killed microorganisms, as of viruses or bacteria, incapable of inducing severe infection by themselves yet capable when inoculated of counteracting the unmodified species. An early example of the utility of such formulations is the vaccine prepared from the cowpox virus and used to inoculate against smallpox. Additional examples include the use of tetanus toxoid to prevent tetanus, whole inactivated bacteria to prevent whooping cough (pertussis), polysaccharide subunits to prevent streptococcal pneumonia, and recombinant proteins to prevent hepatitis B.

In order for a vaccine to induce a protective immune response, it must fulfill three requirements. First, it must include the particular antigen(s) or fragments thereof that will be the ultimate target of protective immunity following vaccination. Second, it must present such antigens in a form which can be recognized by the immune system, i.e. a form that won't be degraded prior to immune recognition. Third, it must activate antigen presenting cells to present antigen to $CD4^+$ T cells, which in turn induce B cell differentiation (without which a strong antibody response cannot be made) and other immune effector functions. This latter function is frequently achieved through use of adjuvants, which are agents that augment the immunologic response to an antigen via nonspecific activation of the immune system.

2.1.3 The Utility of Immunization against Self Molecules

Traditionally vaccination has been considered a means to protect against disease caused by infectious agents. However, the technology has other applications, including control of mammalian fertility, modulation of hormone action, and the prevention or treatment of tumors. As an example which is meant to be illustrative but not exclusionary of other possible examples, one can consider vaccination against human chorionic gonadotropin to prevent or treat cancer.

Treatment of cancer is limited by the fact that success is unpredictable at best if malignancy has spread to lymph nodes and/or other tissues. This process of spreading is called metastasis. Surgery is curative as a primary treatment only if all cancer is removed. Radiation therapy and chemotherapy are toxic, relatively nonspecific, and generally ineffective for metastatic disease. In short, therapy fails and cancer kills because of failure to control recurrent or metastatic disease. Thus in spite of myriad advances in the treatment of primary cancer, survival statistics remain discouraging.

Immunotherapy has been proposed as a complement to the above three conventional approaches to cancer treatment. Vaccines might be able to target cancer more specifically than either radiation or chemotherapy and to prevent or delay recurrent disease by providing continued specific recognition of tumor cells. The topic of tumor immunotherapy is reviewed extensively in the book entitled Biologic Therapy of Cancer, which is edited by Vincent DeVita, Samuel Hellman, and Steven Rosenberg (second edition, 1995, J. B. Lippincott, Philadelphia).

With the exception of virus-specific antigens, tumor associated antigens (TAA) are generally normal antigens that are inappropriately expressed, e.g. in a mutated form or at dysregulated levels as much as 100-fold higher than in normal cells. Importantly, an immune response specific to metastatic tumor cells might be expected to promote destruction of such cells and thus prevent or retard the development of metastatic tumors.

Two factors differentiate cancer vaccines from those against infectious disease agents. First, in vaccination to prevent infectious diseases, the goal is generally to limit the degree of infection rather than to contain it. By contrast, cancer immunotherapy is initiated after rather than before disease is apparent. Second, since TAA's are most often normal tissue components, vaccination against them may induce autoimmunity. For example, vitiligo (skin depigmentation) is routinely observed in patients undergoing regression of melanoma. This is consistent with immune-mediated disease regression resulting from a response against tyrosinase, a melanocyte (and thus melanoma) specific antigen.

Most tumor immunologists now believe that induction of T cell immunity to tumor antigens is of greatest importance and that induction of B cell (antibody) responses are of secondary importance or unimportant. For example, the book edited by DeVita on Biologic Therapy of Cancer places a heavy emphasis on strategies to develop cytotoxic T lymphocyte responses against tumors and discusses antibody-based strategies for antitumor vaccination only with respect to the use of monoclonal antibodies for passive immunization. A second example comes from a 1993 paper entitled "Cancer Vaccines", written by Drew M. Pardoll and published in Trends in Pharmaceutical Sciences (volume 14. pages 202–208). In this paper Dr. Pardoll highlights in his introduction "the emerging principle that T-cell responses, rather than antibody responses, are the primary target of effective antitumor immunization strategies." Finally, Hans Schreiber writing on "Tumor Immunology" (pages 1143–1178) in William Paul's book, Fundamental Immunology, states that "a strong humoral response to tumor antigens does not seem to be correlated with demonstrable resistance of the host to the tumors." Thus there has emerged a principle that T cell immunity provides the key path to effective tumor immunotherapy.

On the other hand it has also been demonstrated that T cell reactivity to self protein antigens can result in numerous life threatening autoimmune diseases. This topic is discussed in a book entitled "The Pathologic Basis of Disease", written by Ramzi S. Cotran, et al. (Fifth edition, 1994, W. B. Saunders, Philadelphia. pages 909–914 and 1326–1328). The topic has also been reviewed more recently on a molecular level by K. Wucherpfennig and J. Strominger ("Selective binding of self peptides to disease-associated major histocompatibility complex (MHC) molecules: a mechanism for MHC-linked susceptibility to human autoimmune diseases". 1995. Journal of Experimental Medicine. volume 181. pages 1597–1601).

Type I diabetes mellitus, for example, is an autoimmune disease afflicting millions of people worldwide. It is the ultimate manifestation of a specific T cell response to peptide antigens of the endocrine pancreas. These antigens are made by the same cells which make insulin, a hormone which is critical to the body's ability to regulate use of sugars for energy. When the insulin producing beta cells of the pancreas are destroyed as a result of specific T cell activation, the individual's blood sugar level can no longer be regulated without an external source of insulin. Although antibodies specific for pancreatic antigens are also found in those suffering from the disorder, specific T cells are thought to be the pivotal inciting factor leading to disease. A virus encountered during childhood has been proposed as the factor initially stimulating specific T cell activation. Chronic, long-term complications occur in blood vessels, kidneys, eyes, and nerves.

A second example of autoimmune disease caused by a specific T cell response is multiple sclerosis (MS). MS is caused by a specific T cell response to myelin components. Myelin is the substance which coats the fastest conducting nerves of the body. Although the initiator of nerve damage is unknown, specific self antigen recognition by T cells has been identified as being central to the disease process. Characteristically MS involves distinct episodes of neurologic defects. The course is variable, ranging from a subclinical form causing no symptoms to a steady, unremitting neurologic deterioration. Demyelination is in any event not thought to be by an antibody-mediated mechanism.

Concepts of breaking self-tolerance then can be summarized as follows. The prevailing view of tumor immunotherapists is that induction of specific T cell responses to self antigens made by cancer cells provides the most effective means to treat malignancy by immunological means. In spite of this, induction of specific T cell responses to self antigens made by diverse cells of the body leads to diverse autoimmune diseases.

2.1.4 Example: Human Chorionic Gonadotropin

Human chorionic gonadotropin (hCG) is a glycoprotein which was originally identified by virtue of its involvement in reproduction; it is produced after fertilization first by the human embryo and then by the placenta. This topic is reviewed in a paper by Soheyla D. Gharib, et al. entitled "Molecular Biology of the Pituitary Gonadotropins" (Endocrine Reviews, 1990, volume 11, no. 1, pp. 177–199).

Specific fragments of human chorionic gonadtrophin (hCG) are detectable on the surface of the cells from all of seventy four human cancer cell lines tested by H. F. Acevedo, et al. ("Expression of membrane-associated human chorionic gonadotropin, its subunits, and fragments by cultured human cancer cells". 1992. Cancer. volume 69. pages 1829–1842). hCG-specific mRNA expression in such cell lines has also been demonstrated (A. Krichevsky, et al. "Immunological detection of membrane-associated human luteinizing hormone correlates with gene expression in cultured human cancer and fetal cells". 1995. Endocrinology. volume 136. pages 1034–1039). Additional evidence exists to suggest that tumor cell expression of hCG may be associated with metastasis (H. F. Acevedo, et al. "Expression of human choriogonadotropin-like material correlates with metastatic phenotype of R3230 AC rat adenocarcinoma". 1987. Cancer Investigation. volume 5. pages 177–185). Since abundant hCG expression is normally pregnancy-associated and restricted to cells of the fertilized ovum, early implanted embryo, and placenta, hCG appears to be a general tumor antigen. This raises the possibility of using immunization against hCG as an antimetastasis treatment.

hCG may confer protection against immune surveillance of tumor cells and/or act as an autocrine growth factor (C. S. August, et al. "Interaction of choriocarcinoma cells and human peripheral blood lymphocytes. Resistance of cultured choriocarcinoma cells to cell-mediated cytotoxicity by mitogen-activated lymphocytes". 1979. Journal of Clinical Investigation. volume 63. pages 428–436; A. Bartocci, et al. "Immunosuppressive activity of human chorionic gonadotrophin preparations in vivo: evidence for gonadal dependence". 1983. Cellular Immunology. volume 82. pages 334–342; and S. Melmed and G. D. Braunstein. "Human chorionic gonadotropin stimulates proliferation of Nb 2 rat lymphoma cells". 1983. Journal of Clinical Endocrinology and Metabolism. volume 56. pages 1068–1070). Similarity between the crystallographically determined structure of hCG and those of known human growth factors (NGF, TGF-b, and PDGF-b) supports the suggestion that hCG functions as an autocrine growth factor in tumor growth (A. J. Lapthorn, et al. "Crystal structure of human chorionic gonadotropin". 1994. Nature. volume 369. pages 455–461). Protection against immune surveillance on the other hand might be associated with a simple charge-mediated repulsion of immune effector cells since hCG bears a high content of negatively charged sialic acid with 16 moles per mole of protein compared with 6 moles per mole of LH. Consistent with this possibility are prior observations that metastatic potential correlates with cell surface sialylation and negative charge (G. Yogeeswaran and P. Salk. "Metastatic potential is positively correlated with cell surface sialylation of cultured murine tumor cell lines". 1981. Science. volume 212. pages 1514–1516; and U. Kim. "On the characteristics of tumor cells and host responses associated with metastatic potential". 1983. 13th International Cancer Congress, Part C, Biology of Cancer. Alan R. Liss, Inc., New York. pages 45–50).

hCG expression stimulates the corpus luteum of the ovary to continue progesterone secretion, which is required for the maintenance of pregnancy. Of the four human glycoprotein hormones (hCG, FSH, LH, and TSH), hCG is the only one synthesized outside of the anterior pituitary. These proteins are all heterodimers; each uses a common alpha subunit, specificity being conferred by the hormone-specific beta subunit. Alpha and beta subunits have, respectively, five and six disulfide bonds. hCG's molecular weight is roughly 38 kD of which about 30% is carbohydrate. hCG, FSH, and TSH each carry four N-linked carbohydrate moieties, two on each subunit. LH also carries two N-linked carbohydrate units on its alpha chain but only one on its beta chain.

The beta subunits of hCG and luteinizing hormone are highly homologous (82%) and differ primarily in that hCG's beta chain has a unique carboxyl terminal peptide extension of 37 amino acids, the CTP. This peptide is unusual in several respects. First, Fiddes and Goodman have postulated that the CTP has likely arisen through loss of a termination codon in an ancestral beta-like gene so that the 3' untranslated region now codes for amino acids (J. C. Fiddes and H. M. Goodman. "The cDNA for the β-subunit of human chorionic gonadotropin suggests evolution of a gene by readthrough in the 3'-untranslated region". 1980. Nature. volume 286. pages 684–687). Second, the sequence AATAAA in the CTP contains both the termination codon of the gene (TAA) and a possible recognition site for mRNA polyadenylation. Third, hCG is the only glycoprotein hormone which carries O-linked carbohydrate moieties, and all four of these are attached to the CTP. Finally, hCG-beta is proline-rich; of thirty seven residues, ten are proline. Circular dichroism studies have revealed that secondary structure of this protein fragment is largely devoid of either alpha helical or beta strand elements (D. Puett, et al. "Circular dichroic and immunological properties of human chorionic gonadotropin-β carboxy terminal peptides". 1982. International Journal of Peptide and Protein Research. volume 19. pages 506–513), and this region is disordered in the published crystal structures.

LH and hCG bind to the same gonadal receptor, and evidence suggests that the CTP of hCG is unimportant to receptor binding. First, CTP-specific antibodies fail to block hCG receptor binding (P. Berger, et al. "Monoclonal antibodies against human chorionic gonadotropin (hCG): II. Affinity and ability to neutralize the biological activity of hCG". 1984. American Journal of Reproductive Immunology. volume 5. pages 157–60). Second, mutant forms of hCG lacking either the CTP or O-linked carbohydrate both bind receptor and induce signal transduction in vitro as well as does wild-type hCG, although their in vivo biological activities are greatly reduced (M. M. Matzuk, et al. "The biological role of the carboxyl-terminal extension of human chorionic gonadotropin beta-subunit". 1990. Endocrinology. volume 126. pages 376–383). This suggests that CTP's role in vivo may be to maintain the observed four-fold greater serum half-life of hCG relative to LH (D. M. De Kretser, et al. "Role of the kidney in the metabolism of luteinizing hormone". 1973. Journal of Endocrinology. volume 58. pages 425–434; and J. R. Sowers, et al. "Metabolism of exogenous human chorionic gonadotrophin in men". 1979. Journal of Endocrinology. volume 80. pages 83–89).

Vaccines based on hCG have been proposed as a means either to control fertility or prevent metastatic cancer. Approaches to development of such vaccines have been pursued using both the entire beta subunit of hCG, as well as the CTP (G. P. Talwar, et al. "Phase I clinical trials with three formulations of anti-human chorionic gonadotropin vaccine". 1990. Contraception. volume 41. pages 301–316; and V. C. Stevens. "Use of synthetic peptides as immunogens for developing a vaccine against human chorionic gonadotropin". 1986. CIBA Foundation Symposium. volume 119. pages 200–225). In the first approach, the antigen is purified and conjugated to a bacterial toxoid then mixed with an adjuvant; in the second, the CTP is synthesized chemically, conjugated to diphtheria toxoid, mixed with muramyl dipeptide, and emulsified in a squalene:mannide monooleate emulsion; antibodies raised against the peptide bind to the native hormone (W. R. Jones, et al. "Phase I clinical trial of a World Health Organization birth control vaccine". 1988. The Lancet. volume 8598. pages 1295–1298; and V. C. Stevens, et al. "Anti-fertility effects from immunization of female baboons with C-terminal peptides of human chorionic gonadotropin". 1981. Fertility and Sterilization. volume 36. pages 98–105).

For anti-fertility vaccination, data from non-human primates indicate that this approach may be effective in preventing pregnancy and that after antibody levels wane, normal pregnancies are observed. In neither of the Phase I clinical trials for fertility control were trial-related abnormalities in the menstrual cycle observed, and a Phase II trial of the whole subunit vaccine protected against pregnancy (G. P. Talwar, et al. "A vaccine that prevents pregancy in women". 1994. Proceedings of the National Academy of Sciences (USA). volume 91. pages 8532–8536). However, antibodies raised against the whole beta subunit of hCG have been shown to cross-react with luteinizing hormone, with which it has considerable homology (O. Singh, et al. "Antibody response and characteristics of antibodies in women immunized with three contraceptive vaccines inducing antibodies against human chorionic gonadotropin". 1989. Fertility and Sterility. volume 52. pages 739–744). The fact that CTP-specific antibodies may remain associated with receptor-bound hCG also raises the possibility of this vaccine inducing oophoritis in recipients (S. Dirnhofer, et al. "Functional and immunological relevance of the COOH-terminal extension of human chorionic gonadotropin beta: implications for the WHO birth control vaccine". 1993. Immunology Today. volume 7. pages 1381–1385). However, no such abnormalities have been observed in non-human primates (V. C. Stevens. "Birth control vaccines and immunological approaches to the therapy of noninfectious diseases". 1990. Infectious Disease Clinics of North America. volume 4. pages 343–354), and if the vaccine's mechanism of action entails decreasing the serum half-life of hCG then this possibility may not become manifest in humans either.

Regarding cancer, prophylactic immunization against hCG prevented metastatic growth of R3230 AC carcinoma cells and the ascites form of Yoshida sarcoma in rats, as well as human lung tumor cells in athymic mice (J. A. Kellen, et al. "Effects of antibodies to choriogonadotropin in malignant growth. I. Rat 3230 AC mammary adenocarcinoma". 1982. Cancer. volume 49. pages 2300–2304; A. Bernardini, et al. "Effect of immunization against human chorionic gonadotropin (hCG) on transplantation of Yoshida ascitic tumour". 1982. Microbiologica. volume 5. pages 383–388; and S. Kumar, et al. "Necrosis and inhibition of growth of human lung tumor by anti-α human chorionic gonadotropin antibody". 1992. Journal of the National Cancer Institute. volume 84. pages 42–47). A Phase Ib trial of an hCG vaccine using the CTP peptide in patients with metastatic cancer has been performed and suggests that this approach may be beneficial (P. L. Triozzi, et al. "Clinical and immunologic effects of a synthetic beta-human chorionic gonadotropin vaccine". 1995. International Journal of Oncology. In press).

There are also other medical needs which can be met by the present invention. Aside from therapy of metastatic and other cancers by use of active specific immunity against tumor specific or tumor associated antigens, there is also a need for a means for control of various disease states or maladies caused or influenced by unusual excesses of certain polypeptides such as gastrin, angiotensin II, or somatomedin. It is believed that this invention meets this need safely and effectively.

2.2 Approaches to the problem

2.2.1 Passive Immunization

It is known that "passive" immunity can be conferred on an animal by administering an antibody formed elsewhere. For instance, patents to Michaelson (U.S. Pat. No. 3,553, 317), Friedheim (U.S. Pat. No. 2,388,260), Reusser (U.S. Pat. No. 3,317,400) and Peterson (U.S. Pat. No. 3,376,198) relate to production of antibodies, which when injected into an animal of a different species or into a human being cause passive immunization. In patents to Fell (U.S. Pat. Nos. 2,301,532 and 2,372,066), the patenteee refers to active immunization using modified histamine in such animals as horses, cows, etc.

The most serious limitation of such approaches stems from the fact that the antibodies are practically produced only in non-human animals. Thus the recipient of such formulations generally produces an active immune response which is specific for the passively administered antibodies. First, this abrogates the effectiveness of the latter via reduced tissue clearance time or direct inhibition of therapeutic effect. Second, this active immune response can lead to life threatening anaphylactic reactions upon subsequent infusions of the passively administered antibodies.

Monoclonal antibodies have been used to try to achieve the same effect. Recent work has focussed on the conjugation of such monoclonal antibodies to cellular toxins or radionuclides. However, all of these formulations suffer from the same drawback as earlier work in passive immunization. In addition, such formulations only utilize the specific binding of one clonal antibody, which may be limited in its affinity. This leads to two additional problems. First, if more than one antibody specificity is needed to achieve a therapeutic effect, then the monoclonal antibody will fail to provide protection. Second, such antibodies may not be sufficiently specific for tumor tissue and thus also result in destruction of normal tissue.

2.2.2 Chemical Conjugation

Carrier proteins can render haptens immunogenic. Haptens are defined as molecules that can bind specifically to an antibody or lymphocyte receptor but cannot induce an immune response, i.e. they are not immunogenic. To evoke an immune response, haptens must generally first be coupled to a carrier molecule, which is usually a heterologous protein. Injection of the hapten-carrier complex into an animal will then give rise to the production by B lymphocytes of antibodies, some of which will be capable of specifically binding to the free, uncoupled hapten molecule. Carrier molecules play more than a transport role, and their ability to stimulate an antibody response against a hapten is thought to be due primarily to their ability to induce a helper T cell response which generates the lymphokines necessary to induce B cell maturation.

Although the earliest haptens studied were small organic molecules, haptenic behavior also applies to larger molecules, such as polypeptide hormones, which are often poorly, if at all immunogenic. To obtain high antibody titers to these hormones it is thus necessary to conjugate them to a carrier molecule. Stevens has developed processes for modifying polypeptides which are not substantially immunogenic to the immune system of mammals so as to make the modified polypeptides more immunogenic (U.S. Pat. Nos. 4,201,770, 4,384,995, 4,526,716, 4,691,006, 4,713,366, 4,762,913, 4,767,842, 4,855,285, and 5,006,334). His inventions also relate to the modified polypeptides so produced, to vaccines containing such modified polypeptides, and for processes for affecting in various ways the metabolism of animals using such modified peptides and vaccines.

The vaccine formulations created by virtue of Stevens' inventions have succeeded in breaking self-tolerance to hCG. However, important limitations of this approach to anti-cancer and anti-fertility vaccination exist. First, covalent coupling of the peptide to DT is inherently variable, and such variation has been demonstrated to affect vaccine potency. Second, injection of the chemical conjugate alone is insufficient to engender an immune response versus the self antigen. Repeated injections combining both the conjugate and a strong adjuvant such as muramyl dipeptide (MDP) are needed to engender a strong peptide-specific immune response (W. R. Jones, et al. "Phase I clinical trial of a World Health Organization birth control vaccine". 1988. The Lancet. volume 8598. pages 1295–1298). Emulsions containing the chemical conjugate and MDP adjuvant have also been problematic due to their instability, necessitating preparation at time of injection and painstaking quality assurance to ensure successful preparation of the emulsion before injection. Furthermore, since antibody levels in most subjects wane roughly six months after immunization, booster injections must be administered every six months in order to maintain effective levels of circulating antibody. Hypersensitivity to the DT carrier has already been observed and precludes use of the vaccine by many people. Pain and sterile abcess formation at the site of injection have also been reported (P. L. Triozzi, et al. "Clinical and immunologic effects of a synthetic β-human chorionic gonadotropin vaccine". 1995. International Journal of Oncology. In press). Finally, the process of chemical synthesis and conjugation is expensive. Thus this means for self-immunization suffers from shortcomings of chemical variability, need for additional adjuvants, unstable emulsions, side effects, and expense of manufacture.

2.2.3 Biological Response Modifiers

Biological response modifiers (BRM's) stimulate the immune system without specificity. Experimentation in their use dates to the 19th century observation that infectious empyemas occassionally led to resolution of a tumor. William Coley reasoned in the late nineteenth century that tumors would be viewed as foreign if the immune system was sufficiently activated; he subsequently developed a collection of heat-killed bacteria with which to treat cancer patients. The property of non-specific immune stimulation is shared by BRM's and adjuvants. Indeed, the terms are in this sense interchangeable.

With respect to cancer immunotherapy, two types of BRM stand out: BCG and cytokines. BCG (Bacille de Calmette et Guérin) is a live attenuated bovine tubercle bacillus possessing nonspecific, immunostimulating properties. It is now F.D.A. approved for use as a prophylactic measure against tumor recurrence following endoscopic resection of superficial bladder cancer. Intravesical instillation is thought to lead to tumor cell killing by either macrophages or T lymphocytes. The response to BCG is immunologically non-specific in that it seems to involve a general activation of the immune system. Efficacy is dependent on both a limited tumor burden and patient immunocompetence.

Similarly, cytokines lead to lymphocyte activation by virtue of altering the cellular environment of antigen presentation. They can thus act as adjuvants for tumor antigens presented by whole tumor cells, tumor cell lysates, or specific tumor cell antigens. The specific antigen presented with cytokines must still carry its own helper T cell epitopes in order to stimulate a high titer B cell (antibody) response.

Several cytokines have shown promise for treatment of cancer. Alpha-interferon is F.D.A. approved for treatment of hairy cell leukemia. GM-CSF and IL-2 have also received favorable attention. GM-CSF supports proliferation of polymorphonuclear granulocytes (neutrophils) and monocytes, in addition to activating mature cells of the same lineages to become tumoricidal and phagocytic in vitro. IL-2 stimulates proliferation and activation of T lymphocytes.

The primary drawbacks of cytokine based cancer immunotherapy involve non-specificity, systemic toxicity, and expense. Cytokines by themselves provide no specificity of response since they include neither B nor T cell-specific epitopes. With respect to toxicity, infusion of IL-2, for example, leads to the capillary leak syndrome and lymphocytic infiltration of visceral organs (J. P. Siegel and R. K. Puri. "Interleukin-2 toxicity". 1991. Journal of Clinical Oncology. volume 9. pages 694–704). Finally, efforts to express cytokines in recombinantly manipulated tumor cells or parts thereof require logistically cumbersome and expensive amounts of skilled labor, research infrastructure, and disposable plasticware.

2.2.4 Crux of the Problem

The crux of the problem described above is that induced, therapeutically useful, anti-self immunity must straddle the balance between an insufficient response and induction of harmful autoimmunity.

Ample experimental evidence points to the facts that in order for an active, specific antibody immune response to occur against a protein antigen, three key requirements of the immunization must be met. First, the critical antibody (B cell) epitopes to be immunized against must be presented in an intact form to the immune system. Second, the vaccine formulation must contain peptide T cell epitopes which will induce the cytokine response required from T cells in order for B cell differentiation to occur. Finally, appropriate adjuvants must be included in the vaccine formulation in order for processing and presentation of T cell epitopes by specialized antigen presenting cells such as macrophages and dendritic epidermal cells to occur. Such processing and presentation is necessary in order for a helper T cell response to be initiated.

A T cell response to a self antigen, however, is troublesome for three reasons. First, it may first be difficult to establish as delineated in Section 2.1.1. Second, once self-tolerance is broken, an uncontrolled T cell response may lead to autoimmunity. For example, fertility regulation vaccines targetted at the zona pellucida of the egg have failed since they inevitably induce oophoritis (inflammation of the ovary). Finally, even if a T cell response is achieved, it won't help in situations where an antibody response provides a protective function.

My invention addresses this problem by incorporating foreign (non-self) T cell epitopes and the natural adjuvant properties of microbial gene products into vaccines which incorporate all three of the above requirements into a single vaccine formulation.

2.3 Recombinant approaches to the problem 2.3.1 Advantages of Recombinant DNA in Addressing the Problem One of the most important applications of recombinant DNA technology is in the production of safe vaccines against infectious diseases and the synthesis of defined proteins against which antisera can be raised for experimental, industrial, and diagnostic purposes.

The present invention relates to techniques for producing fused proteins or other microbial products which are useful as immunogens for therapeutic and preventive vaccines that succeed in overcoming normal tolerance to self proteins. A specific example described involves expression of a gene for a fused protein consisting of heat-labile enterotoxin B subunit (LTB) and a protein heterologous to heat-labile enterotoxin (LT), using recombinant techniques.

Such formulations contain a genetic linkage between microbial helper T cell epitopes and one or a group of "self" protein epitopes. Inclusion of prokaryotic helper T cell epitopes facilitates both induction of a high titer antibody (B cell) response and the development of immunological memory, which is also mediated primarily by T cells. In addition, the demonstrated adjuvant properties of numerous microbial gene products free such vaccines from the need for additional adjuvants.

My invention offers four primary advantages over prior art. First, recombinant DNA technology enables consistent production of a defined vaccine formulation. This is superior to peptide synthesis and chemical conjugation, which lead inevitably to variability in preparation that can affect vaccine potency. Second, due to the natural action of microbial products, my invention precludes the need for additional adjuvants such as muramyl dipeptide in the final vaccine formulation. Third, recombinant protein expression enables lower costs of vaccine manufacture relative to the significant expense of peptide synthesis and chemical conjugation. Finally, recombinant expression of self proteins in a form linked to microbial products may facilitate the introduction of such formulations via mucosal immunization. This could feasibly include oral, nasal, or rectal administration and is not possible with the chemical conjugates described above.

2.3.2 Novelty of Recombinant DNA Approach

Recombinant vaccines to break immunological self-tolerance as outlined in this application are novel from the following three perspectives.

First, there is a precedent which establishes that recombinant presentation of any given protein is empirical, and failures in every one of the strategies detailed below are abundant. LTB, for example, fails generally as a fusion protein partner for generation of novel immunogens. This failure is likely due to instability of the antigen linked to LTB. An example of this comes from U.S. Pat. No. 5,241,053 (Fused Proteins Comprising Glycoprotein GD of HSV-1 and LTB) in which no quantitative or physical data was shown regarding either stability or immunogenicity of the fusion gene constructed.

Second, there is a precedent which establishes that recombinant presentation of self antigens may be effective as a means to induce rather than break immunological tolerance. Induction of immunological tolerance would be useful for the purpose of treating autoimmune disease. This implies that such a strategy would fail to break immunological self-tolerance In a paper by Jia-Bin Sun, et al. entitled "Cholera toxin B subunit: an efficient transmucosal carrier-delivery system for induction of peripheral immunological tolerance" (November 1994, Proceedings of the National Academy of Sciences USA, volume 91, pp. 10795–10799), the authors describe experiments in which oral delivery of a chemical conjugate between LTB and an unrelated antigen resulted in suppression of the specific immune response to the unrelated antigen.

Third, as detailed in Section 2.1.3, there is a precedent that effective tumor immunotherapy must be based on breaking T cell tolerance to a self antigen. In this view it is direct cytolytic action of T cells which results in tumor cell elimination. My strategy on the other hand is based on the presentation of self antigens in a form which is genetically linked to foreign helper T cell epitopes. Thus while a T cell response to the self protein may occur, it is not necessary for the development of an antibody response.

2.3.3 Overview of Recombinant Approach to the Problem

In current recombinant DNA procedures, specific DNA sequences are inserted into an appropriate DNA vehicle, or vector, to form recombinant DNA molecules that can replicate in host cells. Circular double-stranded DNA molecules called plasmids are frequently used as vectors, and the preparation of such recombinant DNA forms entails the use of restriction endonuclease enzymes that can cleave DNA at specific base sequence sites. Once cuts have been made by a restriction enzyme in a plasmid and in the segment of foreign DNA that is to be inserted, the two DNA molecules may be covalently linked by an enyzme known as a ligase. General methods for the preparation of such recombinant DNA molecules have been described by Cohen and Boyer in U.S. Pat. No. 4.237,224. Other useful general methods have been described by Collins and Hohn in U.S. Pat. No. 4,304,863. Because of their broad utility, these patents are hereby incorporated by reference.

Once prepared, recombinant DNA molecules can be used to produce the product specified by the inserted gene sequence only if a number of conditions are met. Foremost is the requirement that the recombinant molecule be compatible with and thus capable of autonomous replication in the host cell. Much recent work has utilized *Escherichia coli* (*E. coli*) as a host organism because it is compatible with a wide range of recombinant plasmids. Depending upon the vector/host cell system used, the recombinant DNA molecule is introduced into the host by transformation, transduction, or transfection.

Detection of the presence of recombinant plasmids in host cells may be conveniently achieved through the use of plasmid marker activities, such as antibiotic resistance. Thus a host bearing plasmid coding for the production of an ampicillin-degrading enzyme can be selected from unaltered cells by growing the host in a medium containing ampicillin. Further advantage may be taken of antibiotic resistance markers where a plasmid codes for a second antibiotic-degrading activity, at a site where the selected restriction endonuclease makes its cut and the foreign gene sequence is inserted. Host cells containing properly recombinant plasmids will then be characterized by resistance to the first antibiotic but sensitivity to the second.

The mere insertion of a recombinant plasmid into a host cell and the isolation of the modified host will not in itself assure that significant amounts of the desired gene product will be produced. For this to occur, the foreign gene sequence must be fused in proper relationship to a signal region in the plasmid for DNA transcription called a promoter. Alternatively, the foreign DNA may carry with it its own promoter, as long as it is recognized by the host. Whatever its origin, the promoter is a DNA sequence that directs the binding of RNA polymerase and therefore "promotes" the transcription of DNA to messenger RNA (mRNA).

Given strong promotion that can provide large quantities of mRNA, the ultimate production of the desired gene product will be dependent upon the effectiveness of translation from mRNA to protein. This, in turn, is dependent upon the efficiency of ribosomal binding to the mRNA. In *E. coli*, the ribosome-binding site on mRNA includes an initiation codon (AUG) and an upstream Shine-Dalgarno (SD) sequence. This sequence, containing 3–9 nucleotides and located 3–11 nucleotides from the AUG codon, is complementary to the 3' end of *E. coli* 16S ribosomal RNA (rRNA) (Shine, J. and Dalgarno, L. "Determinant of cistron specificity in bacterial ribosomes". 1975. Nature. volume 254. pages 34–38). Apparently ribosomal binding to mRNA is facilitated by base pairing between the SD sequence in the mRNA and the sequence at the 16S rRNA 3' end.

Methods for the expression of heterologous DNA in a microorganism are now known. In principle, the heterologous DNA coding sequence is inserted in a DNA transfer vector at a point located within an expressible operon. The inserted sequence must be in a reading frame phase with the coding sequence of the operon and oriented in the same direction with respect to translation. When the conditions are met, translation of the operon results in "readthrough" to the inserted coding sequence such that the protein produced is a fusion protein comprising an N-terminal amino acid sequence coded by the expressible operon, followed by an amino acid sequence coded by the insert. An early example of this is provided by B. Polisky, et al. ("A plasmid cloning vehicle allowing regulated expression of eukaryotic DNA". 1976. Proceedings of the National Academy of Sciences (USA). volume 73. pages 3900–3904). Numerous expressible operons have been employed, including insertion in the beta-galactosidase gene, the beta-lactamase gene, and many others.

Correct presentation of the antigen to an animal or human immune system is a key requirement for an effective subunit vaccine or immunogen. Presentation has been a major problem with potential vaccines and immunogens made by recombinant DNA technology as well as for those based on chemically synthesized epitopes. An ideal immunogen would be a polymer of multiple antigenic determinants assembled in the correct conformation into a high molecular weight carrier possessing multiple helper T epitopes. Such an ideal immunogen would also incorporate adjuvant activity into the formulation so that presentation of helper T cell and B cell (antibody) epitopes would occur effectively.

These requirements are rarely achieved by the simple synthesis of monomeric proteins by recombinant DNA technology or chemical synthesis. They are, however, achieved by recently developed recombinant strategies in vaccine development.

2.3.4 *Escherichia coli* Labile Toxin Subunit B (LTB)

Enterotoxigenic *Escherichia coli* produces two diarrheagenic enterotoxins. One is a relatively low molecular weight species of 2,000 daltons. This species, which survives treatment at 100 degrees centigrade, is referred to as the heat-stable toxin (ST). A second toxin that is heat-labile (LT) is remarkably similar to cholera toxin. LT has been described in detail in U.S. Pat. Nos. 4,666,837, 4,808,700, 5,079,165, 5,241,053, 5,268,276, and 5,308,835, which are incorporated as references herein.

LT is part of a family of toxins that catalyze intracellular ADP-ribosylation of GTPases, leading to increased cAMP production, ion secretion, and ultimately cell toxicity. LT consists of one A subunit of 27,000 daltons and five B subunits, each of 11,600 daltons. The A subunit possesses catalytic activity. The B subunit, which binds GM1 gangliosides present on all mammalian cells, is responsible for targetting the A subunit to cells. After binding of B subunits to glycolipids on a target cell, a fragment of the A subunit is translocated across the cell membrane to the cytoplasm, its site of action. Both subunits are synthesized as precursors, and the $AB_5$ complex, which is assembled in the periplasm, may be released as part of outer membrane fragments. Bacteria of the species Vibrio secrete recombinantly expressed LT (as well as cholera toxin) directly into liquid media.

Surfactants have been used for enhancing absorption of foreign or bioactive substances (proteins) through nasal mucosa tissues. With that view, the ability of the B subunit to bind GM1 gangliosides makes LTB a desirable vaccine component to induce protective antibodies against numerous infectious disease agents. LTB and the related cholera toxin B subunit (CTB) have thus been studied for the purpose of immunization with foreign antigens orally or through nasal mucosa tissues. Consequently, it has been demonstrated that heterologous proteins can be expressed as fusion proteins with LTB and that such fusion proteins can be used to induce a specific immune response against the heterologous protein (T. O. Nashar, et al. "Current progress in the development of the B subunits of cholera toxin and *Escherichia coli* heat-labile enterotoxin as carriers for the oral delivery of heterologous antigens and epitopes". 1993. Vaccine. volume 11. pages 235–240; and J. B. Dale and E. C. Chiang. "Intranasal immunization with recombinant group A streptococcal M protein fragment fused to the B subunit of *Escherichia coli* labile toxin protects mice against systemic challenge infections". 1995. The Journal of Infectious Diseases. volume 171. pages 1038–1041).

Adjuvanticity of LT for unlinked antigens administered orally has been associated with the presence of an active A subunit. Yet the fact that specific immune responses have been raised against antigens of several infectious agents linked as fusion proteins to LTB argues that as long as the antigen of interest is linked to LTB as a fusion protein, the catalytic (and disease producing) A subunit need not be present. This may be because LTB itself adheres in the gut lumen to epithelial M cells, which are specialized to facilitate contact between luminal antigens and gut associated lymphoid tissue (GALT). The entry to GALT of antigens not linked to LTB is not facilitated without the concomitant damaging effects to overlying epithelium produced by the A subunit's catalytic activity. In this sense LTB possesses adjuvant activity since it facilitates nonspecific antigen presentation to B and T cells in the gut and other tissues.

LTB thus serves as a paradigm for recombinant vaccine vectors. Such vectors are a source of both non-self helper T cell epitopes and adjuvant activity to enable effective antigen presentation.

The prospect of using LTB as a carrier for heterologous antigens has been thwarted by the surprisingly poor immune responses to most attached antigens. Such poor responses may be due to two primary factors. First, antigens linked to LTB may be degraded by extracellular proteases before being recognized by the immune system. Second, the antigen linked to LTB may be degraded prior to egress of the protein from *E. coli*. This may be due in particular to the nature of the "linker" peptide between LTB and the added antigen. Third, ability of recombinantly expressed fusion proteins based on LTB to form pentamers is likely of particular importance for the adjuvant activity of such formulations. In most published reports on such fusion proteins, pentamer formation is not assessed. To summarize, construction of fusions based on LTB has to date been largely empirical, and it is likely that linker peptides which are either unduly short or have multiple hydrophobic amino acid residues may either predispose to premature degradation or inhibit pentamer formation of the antigen linked to LTB.

A frequent drawback of analyses of such fusion proteins is that there is a failure to demonstrate that the fusion protein produced is full-length, that it is stable, and that it forms pentamers (as does the wild-type LTB protein). For example, in U.S. Pat. No. 5,241,053 describing "Fused proteins comprising glycoprotein gD of HSV-1 and LTB", the inventors neglect to show data describing any of the above mentioned features.

Two recent publications have surveyed the literature regarding use of LTB or cholera toxin B subunit (CTB) as carriers for antigens of other infectious disease agents (Toufic O. Nashar, et al., "Current progress in the development of the B subunits of cholera toxin and *Escherichia coli* heat-labile enterotoxin as carriers for the oral delivery of heterologous antigens and epitopes", 1993, Vaccine, Volume 11, pp. 235–240; and Jan Holmgren, et al., "Cholera toxin and cholera B subunit as oral-mucosal adjuvant and antigen vector systems", 1993, Vaccine, Volume 11, pp. 1179–1184). In neither of these literature surveys is there any mention or suggestion of the use of LTB, CTB, or any other recombinant vaccine vector for the purpose of breaking immunological self-tolerance. The focus is rather on use of these proteins to boost the response against other infectious disease agents.

Finally, in a paper by Jia-Bin Sun, et al. entitled "Cholera toxin B subunit: an efficient transmucosal carrier-delivery system for induction of peripheral immunological tolerance" (November 1994, Proceedings of the National Academy of Sciences USA, volume 91, pp. 10795–10799), the authors describe experiments in which oral delivery of a chemical conjugate between cholera toxin B subunit (CTB) and an unrelated antigen resulted in suppression of the specific immune response to the unrelated antigen. CTB and LTB are essentially identical structurally and as vaccine carriers. Specific suppression of the immune response is the opposite of breaking self-tolerance. This argues that use of recombinant vaccine vectors such as LTB to carry self proteins in order to break immunological self-tolerance is contrary to prevailing standards in the art.

2.3.5 Hepatitis B virus Core Antigen

Hepatitis B virus (HBV) is the prototype member of the hepadnaviridae family. These are small reverse transcribing viruses with a partially double stranded DNA genome. The nucleocapsid or core antigen (HBcAg) of HBV is a highly immunogenic particle composed of 180 subunits of a single protein chain. It has been used successfully as a carrier for several peptidic epitopes covalently linked by genetic engineering as well as for chemically coupled protein antigens. HBcAg can function as a source of T cell epitopes and possesses adjuvant activity. In addition, it is non-cytotoxic in humans and can be produced cheaply in recombinant *E. coli*.

In a paper by Florian Schodel, et al., entitled "Hepatitis B virus core particles as a vaccine carrier moiety", published in International Reviews of Immunology (1994, Volume 11, pp. 153–165), the authors survey literature regarding the possibilities of using HBcAg as a vaccine carrier. This paper documents that HBcAg is able to provide both non-self helper T cell epitopes and adjuvant activity. Nonetheless much of the literature surveyed is directed to structure and function of the core antigen, especially as it relates to insertion of heterologous epitopes and mechanisms of immunogenicity. Furthermore, only infectious disease agents are named in the document as putative added antigens. No utility of immunization to break self-tolerance is described.

2.3.6 Salmonella

Strains of *Salmonella typhi* made non-virulent in various ways have been developed for use as orally administered, live vaccines to replace the injected, killed-cell vaccine which is fairly effective but causes unpleasant side effects. Strain Ty21a, attenuated by mutations of unknown nature and now in use in many countries including the U.S., is safe and 70% effective but has several shortcomings including the need to give three doses by mouth.

Another kind of attenuated Salmonella strain is expected to be effective even in one oral dose. It is non-virulent because of its requirement for paraaminobenzoic acid (PABA) due to blocks in the aromatic pathway by deletions at ARO (aromatic dependent) loci (S. K. Hoiseth and B. A. D. Stocker. "Aromatic-dependent *Salmonella typhimurium* are non-virulent and effective as live vaccines". 1981. Nature. volume 291. pages 238–239). PABA is not present in vertebrate tissues. Such blocks in strains of the mouse pathogen *S. typhimurium* cause effectively complete attenuation, i.e. no ill effects in mice given 3 million bacteria intraperitoneally whereas as few as 20 bacteria of the parent strain cause fatal infections. Their efficacy as live vaccines in animal models of typhoid fever and the first results of volunteer trials of analogous candidate live-vaccine strains of *S. typhi* suggest that a safe and effective ARO *S. typhi* live vaccine will soon be available (D. M. Hone, et al. "Evaluation in volunteers of a candidate live oral attenuated *Salmonella typhi* vector vaccine". 1992. Journal of Clinical Investigation. volume 90. pages 412–420).

Such strains of attenuated Salmonella can be used to carry genes specifying an antigen against which an immune response cannot otherwise be obtained, as has been done by administering passenger-carrying, aromatic-dependent Salmonella live vaccines to both animals and humans (T. P. Poirier, et al. "Protective immunity evoked by oral administration of attenuated aroA *Salmonella typhimurium* expressing cloned streptococcal M protein". 1988. Journal of Experimental Medicine. volume 168. pages 25–32; and C. Gonzalez, et al. "*Salmonella typhi* vaccine strain CVD 908 expressing the circumsporozoite protein of *Plasmodium falciparum*: Strain construction and safety and immunogenicity in humans.". 1994. Journal Of Infectious Diseases. volume 169. pages 927–931).

In a paper by Lucia Cardenas and John D. Clements, entitled "Oral immunization using live attenuated *Salmo-*

*nella spp.* as carriers of foreign antigens" (1992, Clinical Microbiology Reviews, volume 5, pp. 328–342), the authors survey the literature regarding the possibilities of using attenuated Salmonella to present unrelated foreign antigens to the immune system. The literature surveyed is directed to background on immunization against enteric disease, oral immunization, attenuation of Salmonella strains, and use of such strains to administer antigens of other infectious disease agents. Only infectious disease agents are named in the document as putative added antigens, and no utility of immunization to break self-tolerance is described.

2.3.7 Mycobacteria

*Mycobacterium bovis* BCG, a live attenuated bovine tubercle bacillus, has been used for most of the last century as a tuberculosis vaccine. This bacterium also possesses several properties which make it suited to presentation of protein antigens not endogenous to Mycobacteria. First, multiple vaccination routes using recombinant BCG have been demonstrated to induce humoral responses against the foreign antigen expressed (M. Lagranderie, et al. "Oral immunization with recombinant BCG induces cellular and humoral immune responses against the foreign antigen". 1993. Vaccine. volume 11. pages 1283–1290). Second, previous BCG priming potentiates the antibody response to a foreign antigen expressed by recombinant BCG. Third, the persistence and adjuvant effects of BCG in host tissues may be sufficient to induce CTP-specific antibodies for up to one year at a time, which would reduce the frequency with which such vaccines would need to be administered. Finally, BCG is the most heat stable of live vaccines and is inexpensive to produce.

A *Mycobacterium-Escherichia coli* shuttle vector and several promoters have been developed to drive expression of foreign antigen genes in BCG (M. Ranes, et al. "Functional analysis of pAL5000, a plasmid from *Mycobacterium fortuitum*: construction of a 'mini' *Mycobacterium-Escherichia coli* shuttle vector". 1990. Journal of Bacteriology. volume 172. pages 2793–2797; N. Winter, et al. "Expression of heterologous genes in *Mycobacterium bovis* BCG: induction of a cellular response against HIV-1 Nef protein". 1991. Gene. volume 109. pages 47–54; and A. Murray, et al. "Expression of *Escherichia coli* beta-galactosidase in *Mycobacterium bovis* BCG using an expression system isolated from *Mycobacterium paratuberculosis* which induced humoral and cellular immune responses". 1992. Molecular Microbiology. volume 6. pages 3331–3342). These have been incorporated into both extra-chromosomal and integrative expression vectors, obviating the need for continued presence of antibiotic selection markers in bacteria that would be administered to humans (C. Martin, et al. "Transposition of an antibiotic resistance element in mycobacteria". 1990. Journal. volume 345. pages 739–743; and C. Martin, et al. "Site-specific integration of the Streptomyces plasmid pSAM2 in *Mycobacterium smegmatis*". 1991. Journal. volume 5. pages 2499–2502). Additional methods facilitate screening for expression of secreted recombinant proteins via creation of fusions with alkaline phosphatase, which can later be removed from the recombinant using unique restriction sites.

In separate papers by C. Kenneth Stover, et al. and Brigitte Gicquel in the book entitled Recombinant Vectors in Vaccine Development (edited by Fred Brown, 1994, Developments in Biological Standardization, volume 82, published by Karger, New York, pages 163–178), the authors describe efforts to use BCG as a carrier for antigens of other infectious disease agents. Only infectious disease agents are named in the document as putative added antigens, and no utility of immunization to break self-tolerance is described.

3 SUMMARY OF THE INVENTION

The present invention is a method for breaking self-tolerance to animal proteins by construction of products in which a microbial (non-self) gene product is linked via recombinant DNA technology to a self gene product in such a manner as to enable production of an immune response to the self protein in the same species of animal as that from which the self gene fragment was originally isolated.

Methods and compositions are provided for the cloning and expression in single-cell host organisms of fusion protein genes coding for the non-toxic subunit of the heat-labile enterotoxin (LTB), the carboxyl terminal peptide (CTP) of human chorionic gonadotropin (hCG), and an intervening peptide linker. Also described are methods for the selection and culturing of the modified hosts to produce such fusion proteins, and for the isolation and purification of this product.

The fusion protein thus produced may be utilized by the methods of this invention for a number of important immunological processes. All such processes relate to the breakdown of immunological tolerance to a self protein via linkage to a microbial product. The microbial product is able to provide both the critical helper T cell epitopes and other adjuvant activity required to break self tolerance to the self protein. Such fusion proteins may be formulated for the production of vaccines having utility in veterinary and human medicine.

Unlike all other microbial vaccine products that have been examined, the product of this invention makes use of genetic linkage between microbial (non-self) and self proteins in order to induce a specific immune response against the self molecule. Such an immune response will at least entail production of specific antibody. In addition, T cells specific for the self protein antigen may also be produced although this latter form of reactivity is not likely to occur in response to all antigens so presented and in any event is not the goal of this invention.

This type of linkage endows a single component formulation with both the T cell epitopes and adjuvant activity necessary to induce a specific immune response, as well as the low cost of manufacture afforded by recombinant DNA technology.

The formulations of this invention may be used for a variety of preventive and therapeutic purposes. As an example, they may be used to inhibit or otherwise treat solid tumors (e.g. tumors of the lung, breast, colon, prostate, bladder, rectum, or endometrium) or hematological malignancies (e.g. leukemias, lymphomas) by administration of the vaccine to an animal or human. Administration may be by any of the means which are conventional for pharmaceutical agents, including oral and parenteral means such as subcutaneously, intramuscularly, and intraperitoneally. The compounds may be administered alone or in the form of pharmaceutical compositions containing a vaccine as described herein together with a pharmaceutically accepted carrier appropriate for the desired route of administration. Such pharmaceutical compositions may be combination products, i.e. may also contain other therapeutically active ingredients.

The dosage to be administered to the animal or human will contain an effective immunogenic, tumor inhibiting amount of active ingredient which will depend upon conventional factors including the biological activity of the particular compound employed; the means of administration; the age, health, and body weight of the recipient; the nature and extent of the symptoms; the frequency of treatment; the administration of other therapies; and the effect desired. A typical dose interval between vaccinations will be between once a week and once a year, preferably between once a month and once every six months. A typical immunogenic dose will be about 0.05 to 100 milligrams per kilogram of body weight, preferably 0.5 to 50 milligrams, on oral administration and about 0.01 to 100 milligrams per kilogram of body weight, preferably 0.5 to 30 milligrams, on parenteral administration.

These novel vaccine formulations can be administered in conventional solid or liquid pharmaceutical administration forms, e.g. uncoated or (film-) coated tablets, capsules, powders, granules, suppositories, or solutions. These are produced in a conventional manner. The active substances can for this purpose be processed with conventional pharmaceutical aids such as tablet binders, fillers, preservatives, tablet disintegrants, flow regulators, plasticizers, wetting agents, dispersants, emulsifiers, solvents, sustained release compositions, antioxidants and/or propellent gases (cf. H. Sucker, et al. "Pharmazeutische Technologie". 1978. Thieme-Verlag, Stuttgart). The administration forms obtained in this way normally contain 1–90% by weight of the active substance.

4 OBJECTS AND ADVANTAGES

Prior to the present invention, the only means to break self-tolerance for therapeutic purposes either in humans or in veterinary applications were based on either passive immunization or active immunization via use of synthetic peptide antigens and chemical conjugation to carrier proteins such as diphtheria toxoid. These systems have serious disadvantages. Passive immunization is limited in its efficacy due to the development of antibodies in the recipient which are specific for and abrogate the effectiveness of passively infused antibodies. Chemical conjugation is limited by the variability of the procedure, need for additional strong adjuvants, deleterious side effects, and expense.

Accordingly, several objects and advantages of my invention are as follows. First, numerous microbial products are amenable to genetic linkage to self proteins, and such vaccines incorporate both helper T cell epitopes and adjuvant in the same formulation. Second, several of these microbial products provide for the possibility of mucosal immunization. Third, the products so produced are not subject to the variability in preparation of chemical conjugates. Fourth, the recombinant vaccines to break self-tolerance described herein may be more convenient to administer, either due to the possibility of single immunizations or immunizations less prone to generation of side effects. Fifth, such vaccines are cheaper to manufacture than chemical conjugates.

Further objects and advantages of my invention will become apparent from a consideration of the ensuing description and drawings.

5 BRIEF DESCRIPTIONS OF THE FIGURES

The present invention may be more readily understood by reference to the following figures (not drawn to scale), wherein FIG. 1 presents features of the oligonucleotides used to engineer the CTP gene fragment;

FIG. 4 shows the DNA nucleotide and protein amino acid sequence (one letter code) of the expressed LTB-CTP fusion peptide from the pRE201 plasmid;

Figure 5A:
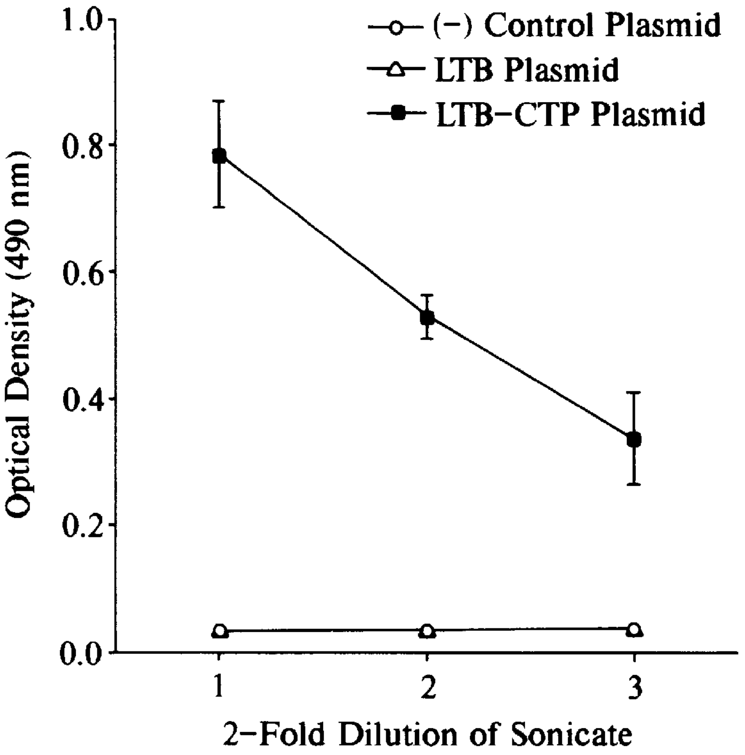
Figure 5B:
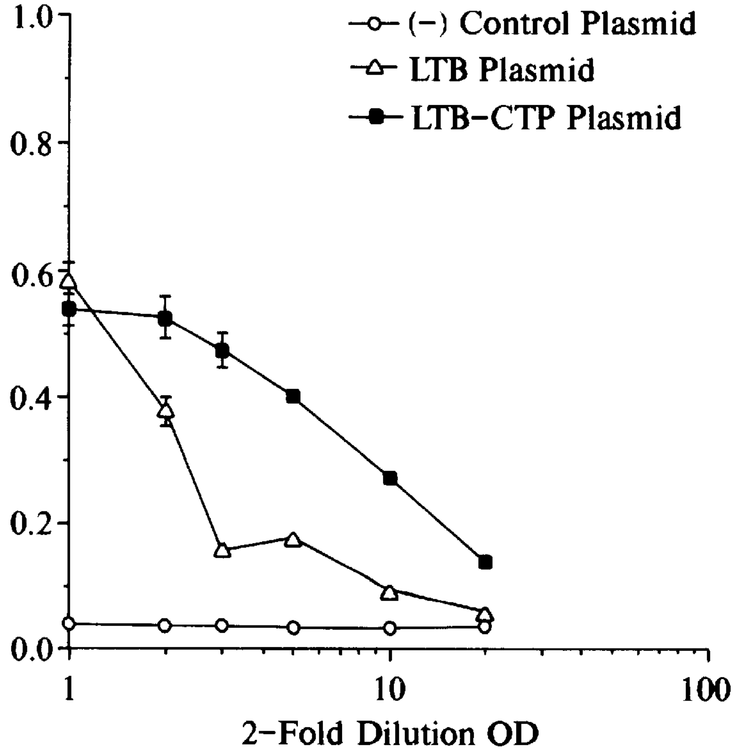

FIG. 5 shows results of ELISA analyses of sonicates from bacteria harboring the plasmids found in FIG. 1; FIG. 5A: GM1 ELISA of bacterial sonicates with anti-CTP rabbit antiserum. FIG. 5B: ELSISA of Sonicates/anti-LT with error bars.

Figure 6:
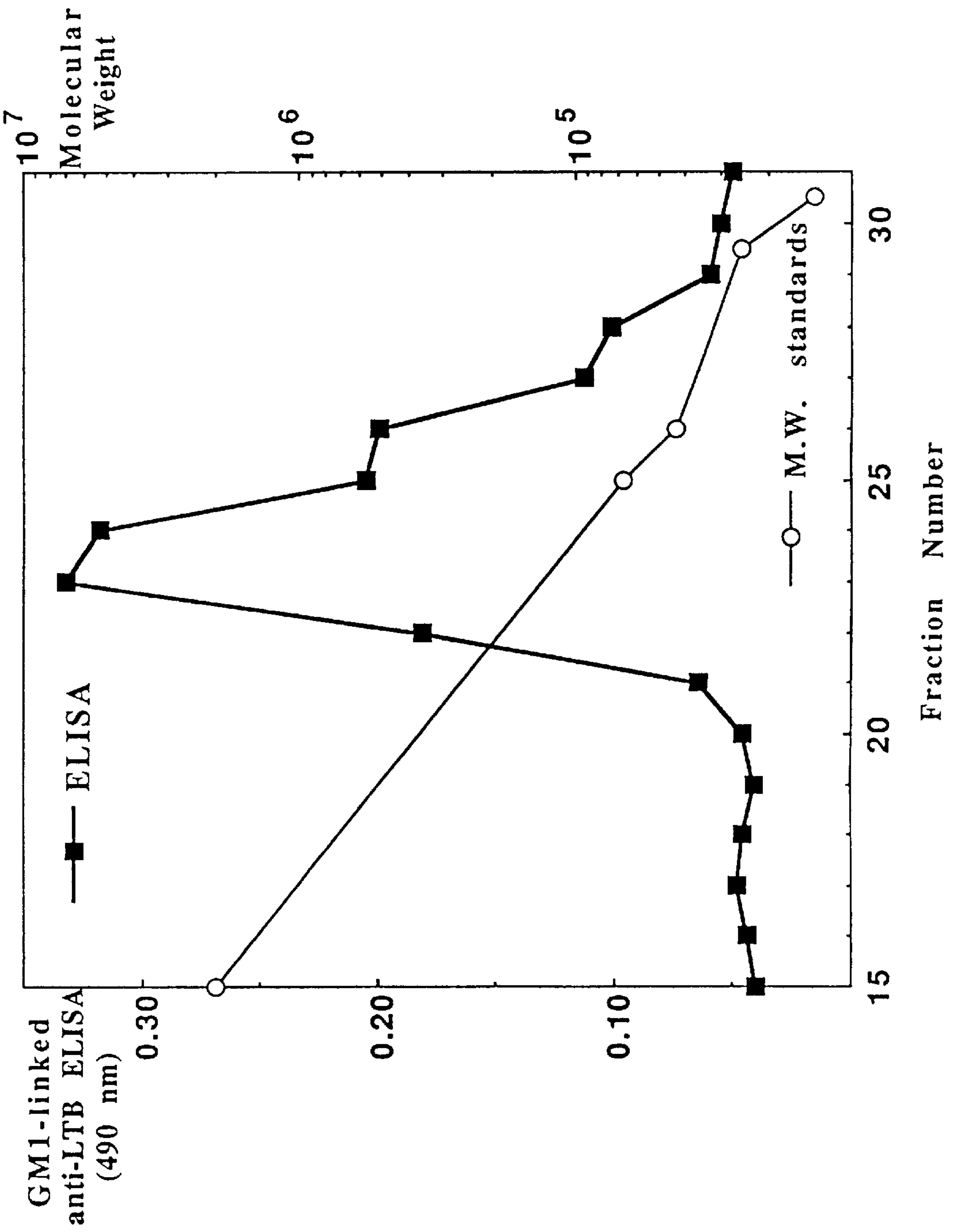
Figure 7A:
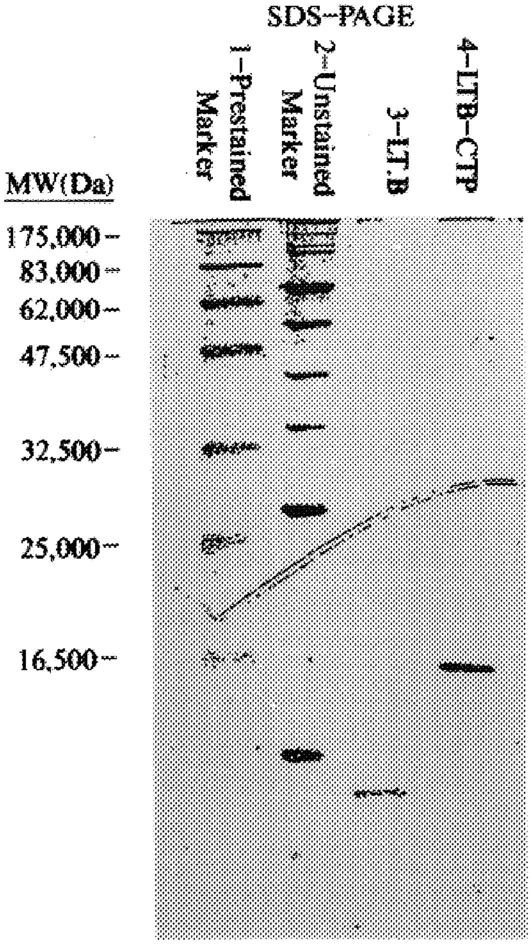
Figure 7B:
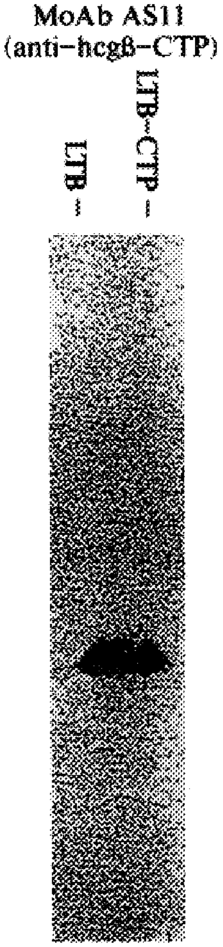
Figure 7C:
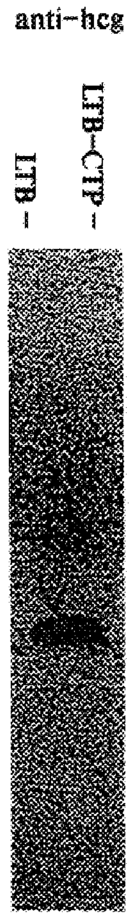

FIG. 6 shows sizing column migration of LTB-CTP fusion protein (ELISA reactivity as black boxes with left hand scale) versus molecular weight size standards (elution profile by UV absorbance, open circles, right hand scale);

FIG. 7 shows sodium dodecyl sulfate—polyacrylamide gel electrophoresis and immunoblotting results of LTB-CTP fusion peptide and LTB alone; FIG. 7A: SDS-PAGE; FIG. 7B: MoAG ASII (anti-hCGβ-CTP); FIG. 7C: Anti-hCG.

Figures 8A, 8B:
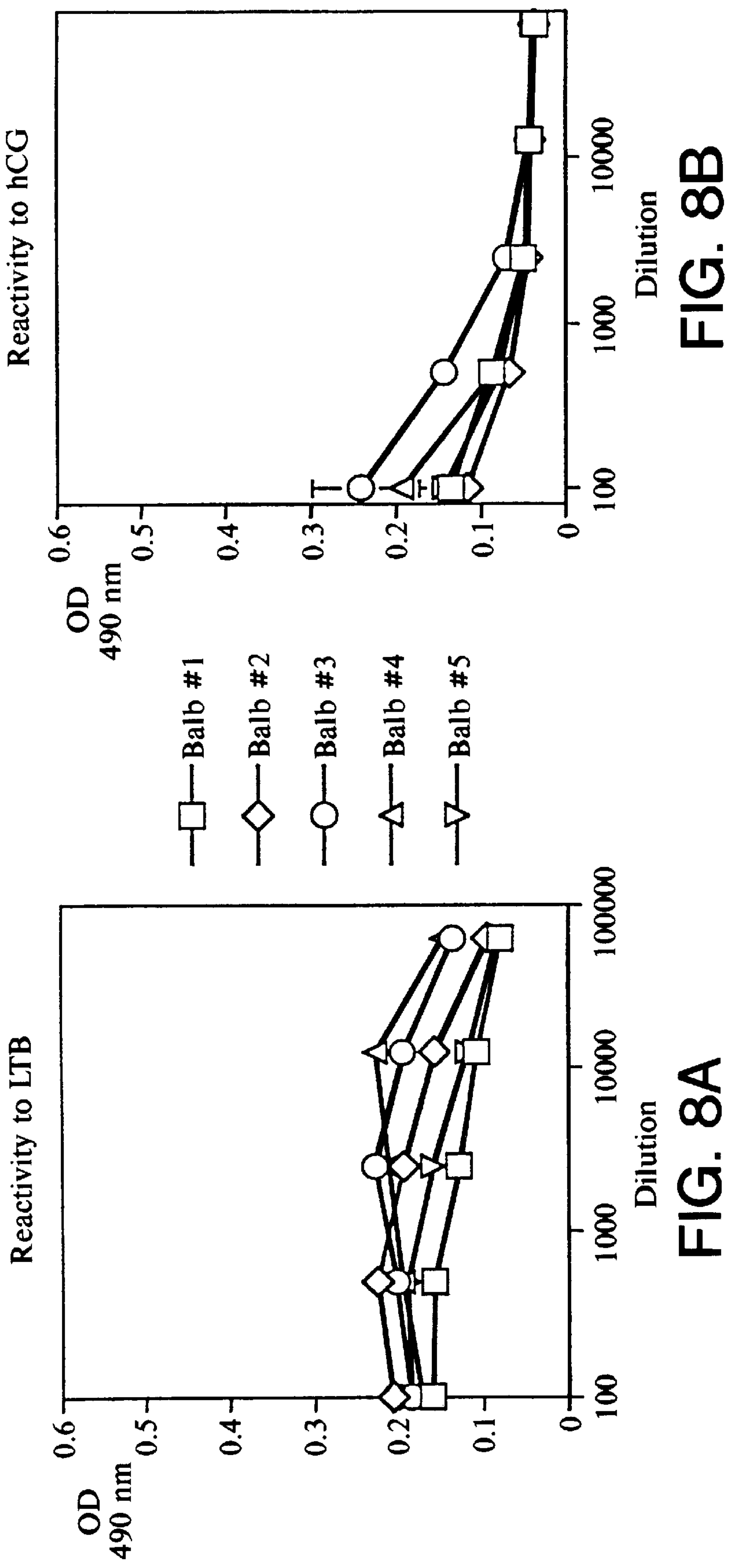

FIG. 8 shows results from ELISA analyses of Balb/c mouse sera following administration of LTB-CTP fusion peptide, each injection with Ribi adjuvant; FIG. 8A: Reactivity to LTB; FIG. 8B: Reactivity to hCG.

Figure 9B:
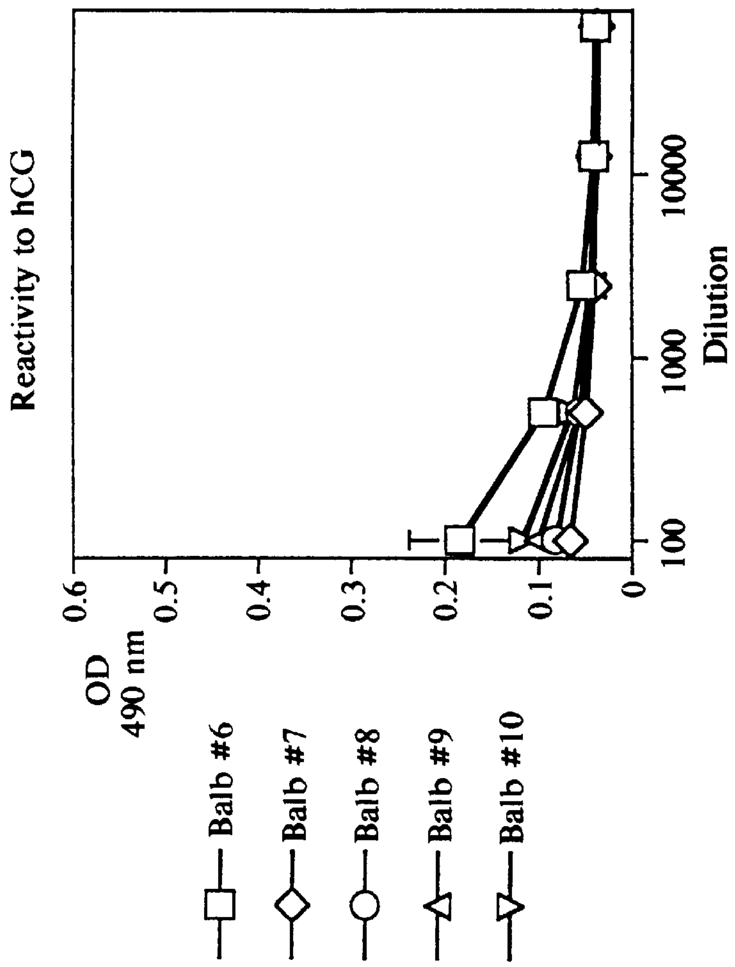
Figure 9A:
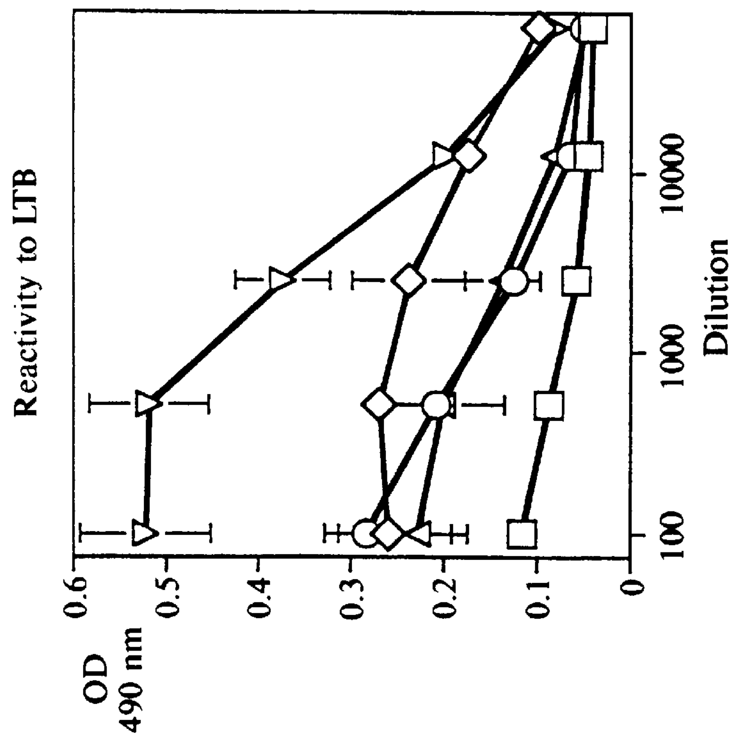

FIG. 9 shows results from ELISA analyses of Balb/c mouse sera following administration of LTB-CTP fusion peptide, each injection without additional exogenous adjuvant; FIG. 9A: Reactivity to LTB; FIG. 9B: Reactivity to hCG.

Figures 10A, 10B:
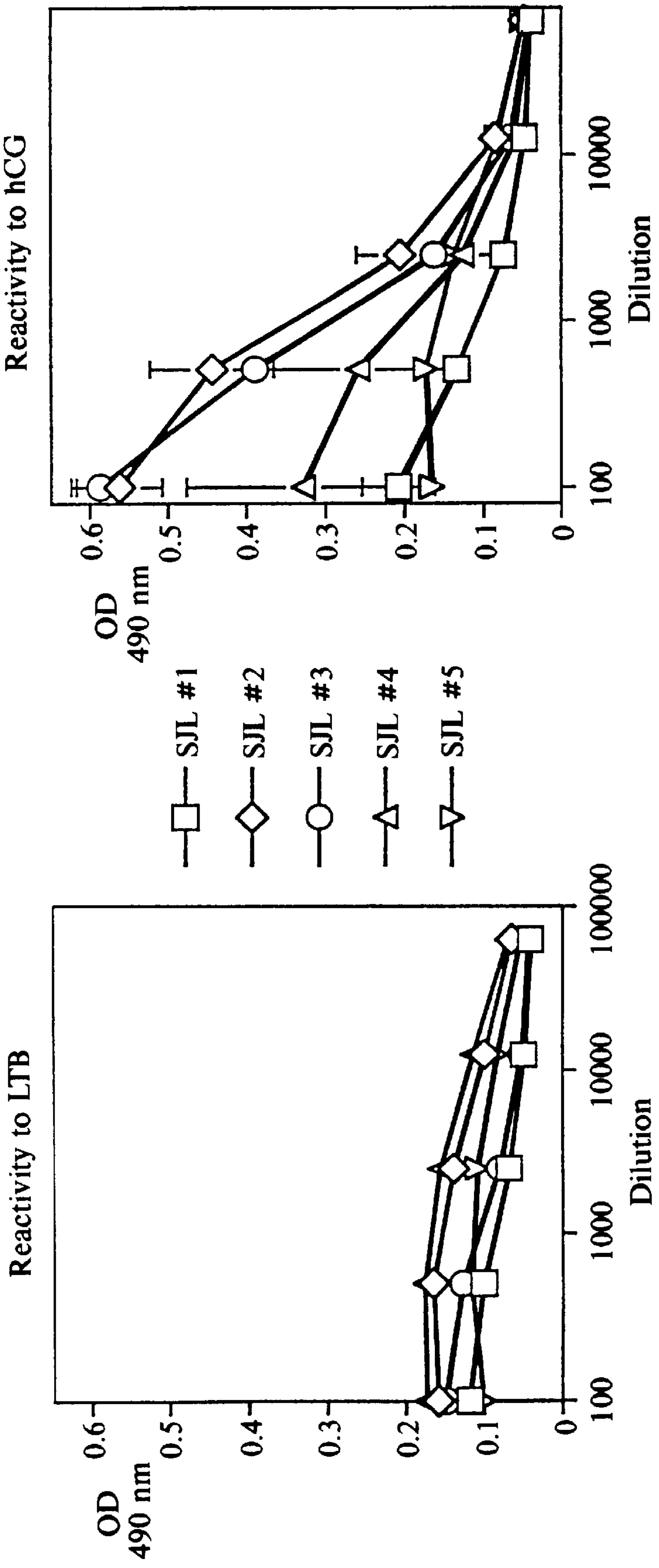

FIG. 10 shows results from ELISA analyses of SJL mouse sera following administration of LTB-CTP fusion peptide, each injection with Ribi adjuvant; FIG. 10A: Reactivity to LTB; FIG. 10B: Reactivity to hCG.

Figures 11A, 11B:
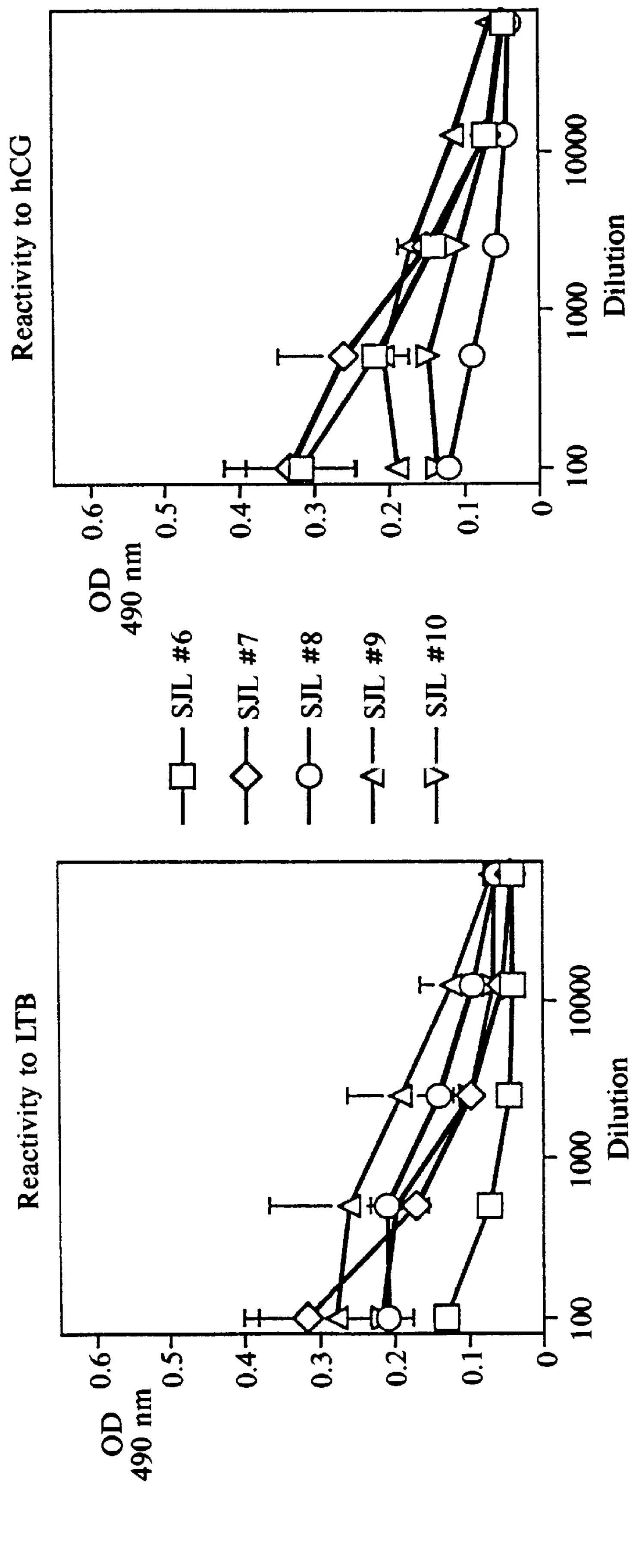

FIG. 11 shows results from ELISA analyses of SJL mouse sera following administration of LTB-CTP fusion peptide, each injection without additional exogenous adjuvant. FIG. 11A: Reactivity to LTB; FIG. 11B: Reactivity to hCG.

Figure 2:
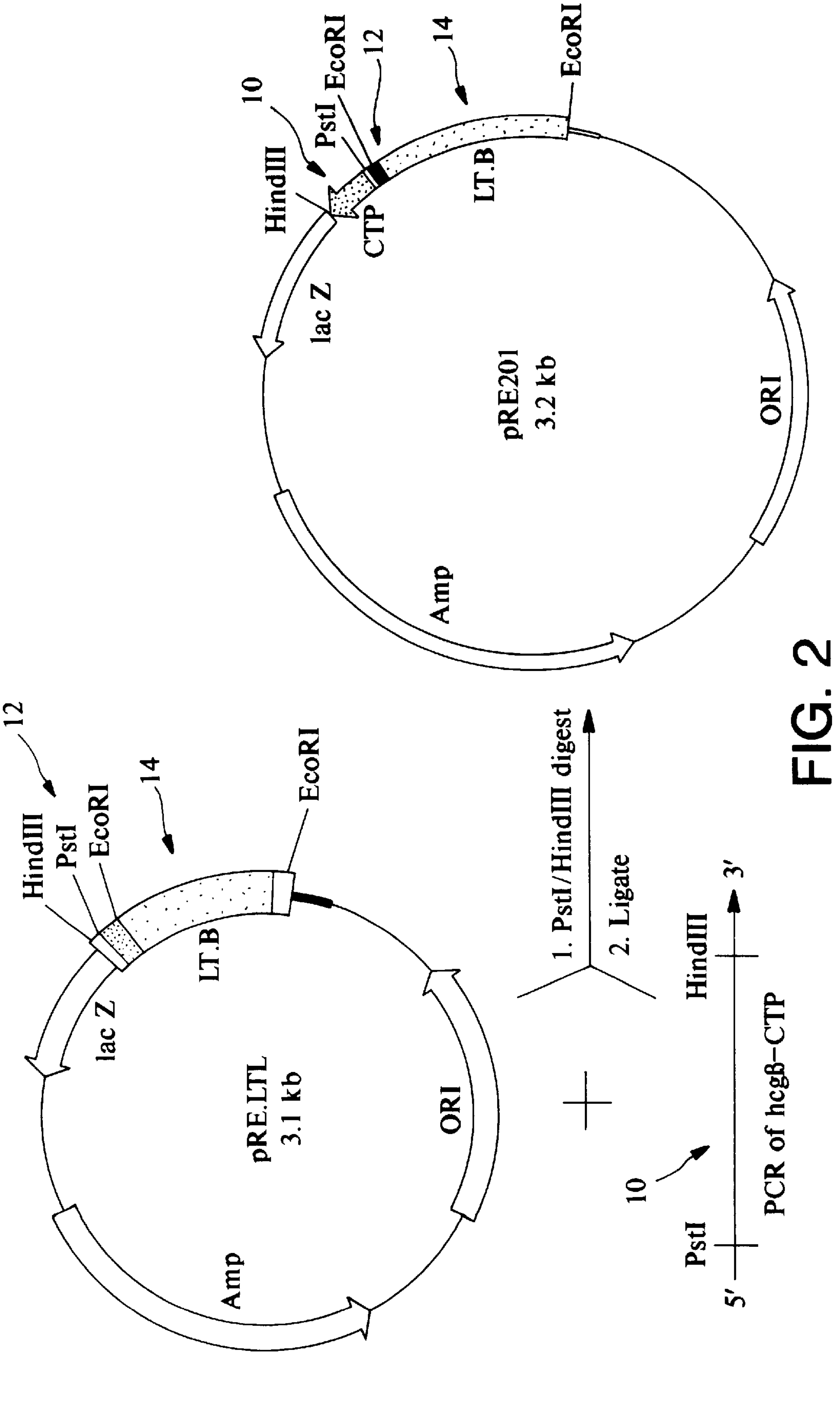
FIG. 2 is a schematic representation of the subcloning strategy to produce pRE201, a fusion protein expression plasmid.

5.1 Reference Numerals (FIGS. 2 & 3)

10 self protein fragment
12 linker peptide
14 recombinant vaccine vector
16 fusion protein pentamer

6 DETAILED DESCRIPTION OF THE INVENTION

I have engineered a fusion protein consisting of *Escherichia coli* heat-labile enterotoxin subunit B (LTB) linked at its C terminus via a nine amino acid linker peptide to the N terminus of the 37 amino acid carboxyl terminal peptide of beta-hCG. This protein is stably expressed in bacteria, forms pentamers of full-length protein chains, and induces hCG-specific antibodies in mice without additional adjuvants.

The primary advantage of the present invention is that it circumvents the chemical variability, complex preparation, side effects, and expense of other vaccines to break self-tolerance that rely on passive immunization, chemical conjugation with additional adjuvant, or lymphokine supplementation.

6.1 Gene construct and Identification

Oligonucleotides encoding the 5' ends of the double stranded 37 amino acid beta-hCG carboxyl terminal peptide (CTP) were synthesized to create by the polymerase chain reaction (PCR) a CTP gene fragment having a Pst I restriction endonuclease site at the 5' end (N-terminus of the protein chain) and a Hind III site at the 3' end (C-terminus). FIG. 1 shows the features of these two oligonucleotide primers used to engineer the CTP gene fragment. The 5' end primer ("CTP-A") substitutes an A for a wild-type T in the first position of the second codon of the CTP. This nucleotide transition changes the encoded amino acid from cysteine to serine. Serine has a hydroxyl side chain which is structurally (and thus immunologically) similar to the sulfhydryl of cysteine, but the former is less reactive chemically. In native hCG the cysteine at this position forms a disulfide bond with another cysteine in the beta chain. However, in the fusion protein this cysteine would be unpaired and thus prone to forming covalent bonds unpredictably with other moieties, hence its replacement by serine. The 3' end oligonucleotide primer ("CTP-B") places a stop codon immediately after the last amino acid codon in the CTP gene fragment.

FIG. 2 shows a schematic representation of the subcloning strategy used to engineer an expression plasmid encoding the LTB-CTP fusion protein. Ten cycles of PCR were performed using the hCG beta chain gene as template (J. C. Fiddes and H. M. Goodman. "The cDNA for the beta-subunit of human chorionic gonadotropin suggests evolution of a gene by readthrough in the 3'-untranslated region". 1980. Nature. volume 286. pages 684–687). Following gel purification and digestion with Pst I and Hind III, this 124 base pair gene fragment was subcloned into the unique Pst I and Hind III sites of the polylinker in plasmid Bluescript (Stratagene; La Jolla, Calif.). The ligation mixture was used to transform *Escherichia coli* strain DH5-alpha to ampicillin resistance. This plasmid is called pBS-CTP.

By similar methods, a PstI-BamHI fragment encoding the CTP epitope was excised from plasmid pBS-CTP and then subcloned into the same unique restriction sites of plasmid pRE.LTL. pRE.LTL is a plasmid which contains the LTB gene in the EcoRI site of the pUC18 multiple cloning site. This multiple cloning site is under the control of the lac operon. The lac operon contains a beta-galactosidase gene promoter which is inducible by IPTG (isopropyl-beta-D-thiogalactoside). The LTB gene clone contains a Shine-Dalgarno site for translation initiation, as well as a signal sequence which is necessary for transport of LTB protein into the periplasm of the recombinant bacterium.

Figures 3A, 3B:
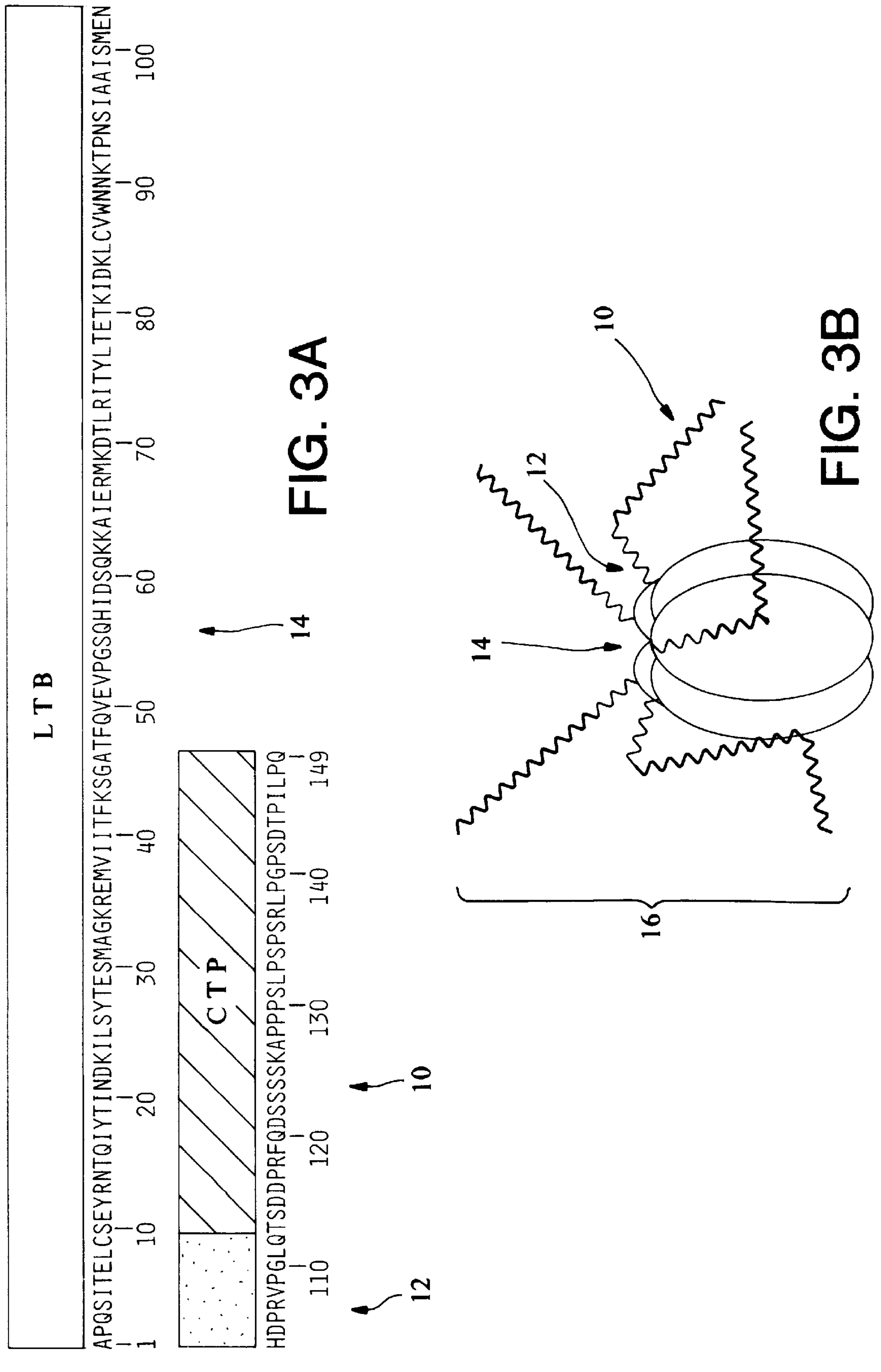
FIG. 3A is a schematic representation of the LTB-CTP fusion protein; 3B is a schematic model of the LTB-CTP fusion protein in expressed, pentameric form.

FIG. 3A shows a schematic representation of the LTB-CTP fusion protein with the LTB portion at the N-terminus and the CTP at the C terminus of a nine amino acid linker. LTB is in white, the linker peptide in grey, and the CTP in black. The fusion protein amino acid sequence is shown in one letter code beneath the diagram.

By subcloning the CTP gene fragment into the Pst I and BamHI sites of the pUC18 polylinker, we were able to create a 27 base pair linker sequence between the LTB gene and the CTP gene fragment. This linker sequence encodes a nine amino acid linker peptide that has a preponderance of hydrophilic amino acids as well as two prolines. Prolines are well known for their ability to break up elements of protein secondary structure, such as alpha-helices and beta strands. Thus I've designed into this fusion protein a linker peptide which should be water soluble and free of induced protein secondary structure. As will be presented below, this design facilitates expression, stability, and hence immunogenicity of the resulting product.

FIG. 3B shows a schematic representation of the pentameric LTB-CTP fusion protein. X-ray crystallography reveals that the five LTB subunits form a pentameric, doughnut-shaped ring and that foreign proteins genetically linked to the carboxyl terminus of LTB would be oriented away from sites involved in glycolipid binding (cell targetting) and pentamer formation (T. K. Sixma, et al. "Crystal structure of a cholera toxin-related heat-labile enterotoxin from *E. coli*". 1991. Nature. volume 351. pages 371–377; and T. K. Sixma, et al. "Lactose binding to heat-labile enterotoxin revealed by x-ray crystallography". 1992. Nature. volume 355. pages 561–564).

The plasmid containing this LTB-CTP fusion protein gene construct is called pRE201. In order to confirm presence and appropriate construction of the insert, both DNA strands of pRE201 were sequenced using the M13 forward and reverse primers. FIG. 4 shows the confirmed fusion protein gene sequence. Nucleotide triplets are shown beneath numbered dashes. Protein sequence is shown in one letter code beneath nucleotide triplets. The LTB leader sequence is numbered from −22 to −1, whereas the processed LTB protein sequence is numbered from 1 to 103. The peptide linker is numbered 104 to 112, and the CTP of hCG is numbered 113 to 149.

Thus we have employed a rational approach to construction of recombinant vaccines based on LTB. This approach is based on three precepts. First, there is genetic linkage between a self protein and a non-self carrier gene product. Second, a linker peptide used to join these moieties should be of a suitable length and should contain primarily hydrophilic amino acid residues. Third, an effective non-self carrier should also possess adjuvant properties in addition to helper T cell epitopes.

Prior to using this protein in immunization experiments we sought to obtain evidence that it is expressed stably in *E. coli*, that it forms pentamers, and that its subunit protein chains are full-length. Although frequently neglected, these characteristics are important because without their fulfillment there is little prospect of reliable specific antibody induction against a self protein by immunization using this process.

Analysis by enzyme-linked immunosorbent assay (ELISA) indicated that the LTB-CTP fusion protein is expressed stably in *E. coli*. Sonicates of bacteria harboring a expression plasmid were tested by ELISA for the ability to bind to $G_{M1}$ gangliosides and be recognized by antisera specific for either the CTP or LTB (FIG. 5). Labels in FIG. 5 are as follows: (−) pUC-18 control plasmid; LTB plasmid: pRE-LTL, a plasmid derived from pUC-18 which expresses the LTB gene driven by the lac promoter; LTB-CTP plasmid: pRE-201, a plasmid derived from pUC-18 expressing the LTB-CTP fusion protein driven by the lac promoter. Dilutions 1, 2, and 3 are 3 mg, 1.5 mg, and 750 ng total protein, respectively. Protein concentrations were derived using the bicinchoninic acid assay. Error bars show standard deviation of mean of three values.

Whereas sonicates of bacteria carrying the pUC expression vector alone were not bound by either antiserum, sonicates of bacteria carrying the pRE.LTL plasmid were bound by anti-LTB antiserum but not anti-hCG serum. Only sonicates of bacteria harboring the pRE201 plasmid which contains the engineered gene encoding the LTB-CTP fusion protein were recognized by both antisera. This indicates both that the CTP epitopes are stably expressed on this fusion protein and that anti-CTP antiserum does not cross-react with LTB.

Pentamer formation of the fusion protein was assessed by size exclusion chromatography. A periplasmic extract at 340 microgram/milliliter containing the LTB-CTP fusion protein was concentrated 8-fold using a Centricon centrifugal microconcentrator. 200 microliters was then loaded onto a Superose 12 (Pharmacia) size exclusion chromatography column. Fractions eluted from the column were tested by GM1-linked ELISA using a goat anti-LTB antiserum (FIG. 6). ELISA reactivity of fractionated LTB-CTP fractions are shown by black boxes and the left hand scale. For comparison results are shown of the elution profile of Molecular Weight (M.W.) standards in open circles against the right hand scale. The peak of LTB-CTP's ELISA reactivity in fractions 23 and 24 corresponds to a molecular weight on the order of 100,000, which is consistent with most of the LTB-CTP protein assuming a pentameric configuration. Additional peaks in fractions 25–26 and 27–28 suggest that lower order multimers may also be present, albeit at much lower concentrations.

The above results demonstrate engineering of a fusion protein gene which links LTB to the CTP of hCG by a nine amino acid linker. This design has been demonstrated to facilitate stable expression of the CTP and pentamer formation by the engineered protein, as indicated by size exclusion chromatography. The question of whether pRE201 fusion protein subunits are full-length or not was addressed by analysis of purified protein.

6.2 Purification of fusion peptide

LTB-CTP fusion protein was grown in *E. coli* strain DH5-alpha harboring the LTB-CTP expression vector. Growth optimization experiments revealed that in rich medium (2xYT), fusion protein accumulated for sixteen hours of culture and that addition of IPTG did not enhance induction of the LTB-CTP construct from the lac operon in pRE201. IPTG is thus omitted from preparation of my invention, further reducing cost of manufacture. Following culture for sixteen hours, bacteria were harvested by centrifugation, sonication, and fractionation via ammonium sulfate precipitation. Harvested protein was purified by affinity chromatography on immobilized D-galactose (Pierce, Rockford, Ill.). Fusion protein was then dialyzed exhaustively with PBS before administration to animals. Yield was determined by absorbance at 280 nm of vaccine in PBS and confirmed by amino acid analysis.

Confirmation of full-length expression of LTB-CTP was determined by several methods as described below.

Samples of LTB-CTP fusion protein were subjected to electrophoresis on 15% polyacrylamide gels (SDS-PAGE), as well as immunoblotting using an anti-CTP monoclonal antibody as well as anti-CTP antiserum. FIG. 7 shows results of these analyses. FIG. 7A shows that LTB and LTB-CTP fusion protein migrate with relative molecular weights of 11,600 and 16,000 daltons, respectively. LTB-CTP migrates with a relative molecular weight slightly higher than that expected due to mass alone. This is likely due to the presence of twelve prolines in the linker and CTP. These prolines constrain the peptide chain's flexibility and thus retard its migration through the gel. A preponderance of LTB-CTP fusion protein is full-length, as shown by SDS-PAGE. Lower intensity bands at lower relative molecular weights may be due to a limited amount of proteolytic degradation of the CTP. Immunoblotting using either monoclonal antibody AS11 (FIG. 7B, specific for the CTP) or polyclonal anti-CTP rabbit antiserum (FIG. 7C) confirms that the full-length fusion protein chain contains CTP epitopes, whereas the LTB chain alone does not.

Size exclusion chromatography of three independently grown and purified preparations revealed essentially identical results to those described in Section 6.1. This confirms that purified LTB-CTP also assumes a pentameric conformation, thus preserving LTB's adjuvant properties.

Appropriate processing of LTB-CTP fusion protein was confirmed by N-terminal sequencing and mass spectrometry of the fusion protein. A sample of purified pRE201 was fractionated by HPLC using a C-4 column. The major peak (#18) was subjected to N-terminal protein sequencing, yielding Ala-Pro-Gln-Ser-Ile-Thr-Glu-Leu, indicating that the LTB leader peptide is excised correctly by the bacteria. Mass spectrometry of the same HPLC peak yielded a single peak from each of two samples with measured mass of 15,572 and 15,574; this matches the predicted molecular mass of the LTB-CTP fusion polypeptide (15,565) within the error range of the instrument.

These data indicate that the LTB-CTP fusion protein is correctly processed by *E. coli* to a form which has the following attributes. First, it should bind to gangliosides effectively in vivo since it has a correctly processed N-terminus, which is known to be important in ganglioside binding. Second, it should possess adjuvant activity since it forms pentamers properly. Finally, it should provide T cell help for an antibody response against the self protein portion since LTB is a known source of multiple helper T cell epitopes. All of these results are in accordance with my predictions of this recombinant vaccine's expected behavior.

6.3 Immunization to Break Self-Tolerance

Formulations of this invention were further tested in pre-clinical assay for in vivo activity which is indicative of clinical immunogenicity. Such assays were conducted with New Zealand White rabbits and three inbred mouse strains. Test formulations were evaluated for their ability to induce antibodies specific for a self protein following administration to these animals.

More specifically, LTB-CTP fusion protein which had been purified from recombinant bacteria was administered into recipient animals. LTB-CTP formulations were administered on up to three occasions at intervals of three to four weeks. Doses ranged from 0.1 to 25 milligrams per kilogram (mg/kg) body weight. Eight to twelve days later blood was collected for analysis of responding antibody levels to both LTB and CTP components of the formulations. Control sera were collected from each animal before immunization.

Two New Zealand White rabbits were immunized on three occasions with LTB-CTP fusion protein plus Ribi adjuvant R-730. Rabbits were immunized with LTB-CTP fusion protein at 0.10–0.40 mg/kg body weight. The first immunizations were with 650 micrograms of fusion protein injected intradermally, intramuscularly, and intraperitoneally. The next two immunizations were with 450 micrograms of fusion protein injected subcutaneously. ELISA titers of these animals' sera following the third injection are found in Table 1.

TABLE 1

Reactivity of Rabbit Sera to LTB and hCG

| animal | reactivity to LTB | reactivity to hCG |
|---|---|---|
| Rabbit 1 | 312,500 | 312,500 |
| Rabbit 2 | 312,500 | 12,500 |

Despite careful engineering of the LTB-CTP fusion protein, it is possible that such a formulation would be degraded quickly in an animal. If this were to happen, then the antibody (B cell) epitopes on the CTP would be separated from the helper T cell epitopes and adjuvant activity of LTB. Thus the experiment summarized in Table 1 was intended as a positive control to demonstrate that the CTP in this formulation, genetically fused to LTB, is still capable of inducing antibodies in rabbits against the native hormone. As the ELISA titers indicate, this is indeed the case.

Groups of five Balb/c ByJ and SJL/J mice were immunized on two occasions with LTB-CTP fusion protein plus Ribi adjuvant R-700. All mice were immunized with doses of LTB-CTP fusion protein at 5–30 mg/kg body weight. Each immunization was with approximately 200 micrograms of LTB-CTP fusion protein injected both subcutaneously and intraperitoneally. Roughly ten days following the second injections, blood was collected. ELISA titers of these animals' sera are found in Table 2.

TABLE 2

Reactivity of Mouse Sera to LTB and hCG following Immunization with LTB-CTP Fusion Protein Plus Ribi Adjuvant

| animal | reactivity to LTB | reactivity to hCG |
|---|---|---|
| Balb/c ByJ #1 | 62,500 | 2500 |
| Balb/c ByJ #2 | 62,500 | 500 |
| Balb/c ByJ #3 | 62,500 | 2500 |
| Balb/c ByJ #4 | 62,500 | 2500 |
| Balb/c ByJ #5 | 62,500 | 2500 |
| SJL/ J #1 | 12,500 | 12,500 |
| SJL/ J #2 | 62,500 | 12,500 |
| SJL/ J #3 | 12,500 | 12,500 |
| SJL/ J #4 | 62,500 | 12,500 |
| SJL/ J #5 | 62,500 | 62,500 |

The data presented in Table 2 are consistent with the results shown in Table 1 and confirm that the CTP portion of the LTB-CTP fusion protein is capable of eliciting antibodies which bind to native hCG. The titers raised in mice are in general somewhat lower than those found in rabbits. This should not be surprising, however, since the rabbits received more protein at more injection sites and a stronger version of Ribi adjuvant than did the mice.

In addition, the mouse titers against native hCG were generally lower than those against LTB. There are probably two reasons for this being the case. First, antisera were raised against the CTP, which lacks the O-linked glycosylation sites of the native hormone. Thus only a fraction of the antibodies induced to the peptide alone are likely to bind the native hormone since some regions of the latter will be obscured by carbohydrate. Second, the hCG ELISA is almost certainly less sensitive than the LTB ELISA. For each native hCG protein molecule there is one CTP, whereas for each LTB pentamer there are five LTB subunits, allowing for more sensitive detection of anti-LTB antibodies. In addition, due to the expense of native hCG, less hormone than LTB was used to coat ELISA microtiter plates (200 nanograms versus 1 microgram per well, respectively). An additional possibility which bears mentioning is that LTB may simply be more immunogenic than the CTP peptide presented in this fusion protein. It is unclear whether this would be due to the fact that LTB is roughly three times the size of the CTP and thus presents more antibody epitopes or a result of LTB's tightly packed pentameric structure, which is probably less susceptible to proteolysis than is the randomly coiled CTP.

Taken together, the data in Tables 1 and 2 indicate that the LTB-CTP fusion protein is likely to be at least as effective in stimulating anti-hCG antibodies as the chemical conjugates described by Stevens. This alone represents an advance since my invention will be cheaper to manufacture. Nonetheless an additional advantage of my invention is that it incorporates into a single vaccine entity both the natural adjuvant activity of numerous identified microbial gene products and the prospect of enabling mucosal immunization.

To test whether or not the LTB-CTP fusion protein is capable of eliciting anti-CTP antibodies without additional exogenous adjuvant, a third trial was conducted. Groups of five Balb/c ByJ, C57BL/6, and SJL/J mice were immunized on three occasions with LTB-CTP fusion protein alone, i.e. without additional exogenous adjuvant. Each immunization was with 300 micrograms of fusion protein in phosphate buffered saline, injected subcutaneously. Roughly ten days following the third injections, blood was collected. ELISA titers of these animals' sera are found in Table 3.

TABLE 3

Reactivity of Mouse Sera to LTB and hCG following Immunization with LTB-CTP Fusion Protein in PBS Alone

| animal | reactivity to LTB | reactivity to hCG |
|---|---|---|
| Balb/c ByJ #6 | 12,500 | 2500 |
| Balb/c ByJ #7 | 62,500 | 500 |
| Balb/c ByJ #8 | 62,500 | 500 |
| Balb/c ByJ #9 | 62,500 | 500 |
| Balb/c ByJ #10 | 62,500 | 2500 |
| C57BL/6 #1 | 100 | 500 |
| C57BL/6 #2 | 100 | 100 |
| C57BL/6 #3 | <100 | 100 |
| C57BL/6 #4 | 100 | 100 |
| C57BL/6 #5 | 100 | <100 |
| SJL/ J #6 | 2500 | 62,500 |
| SJL/ J #7 | 12,500 | 62,500 |
| SJL/ J #8 | 62,500 | 2500 |
| SJL/ J #9 | 62,500 | 62,500 |
| SJL/ J #10 | 62,500 | 12,500 |

Table 3 reveals marked interstrain variation in the antibody responses observed to both LTB and CTP components of the fusion protein. At least some of these interstrain differences are likely due to the MHC haplotype of each mouse strain. MHC haplotype is known to be associated with T cell responses to peptide antigens since it is the MHC molecules which ultimately present peptide antigens to the antigen-specific T cell receptor. As previously discussed, helper T cell activity is necessary for a high titer antibody response to be raised against a protein antigen. Thus the lack of response in C57BL/6 mice to the LTB-CTP fusion protein is consistent with the fact that these mice don't respond to LTB alone either (T. O. Nashar, et al. "Current progress in the development of the B subunits of cholera toxin and *Escherichia coli* heat-labile enterotoxin as carriers for the oral delivery of heterologous antigens and epitopes". 1993. Vaccine. volume 11. pages 235–240). Balb/c ByJ, C57BL/6, and SJL/J mice possess the d, b, and s haplotypes, respectively.

Pre-immune sera of all of the above mice have a titer of less than 100, which was the lowest dilution tested. This confirms that the antibody responses observed are due to immunization with the LTB-CTP fusion protein and not to preexisting antibody reactivity which is specific for either LTB or hCG.

It is unlikely that the CTP peptide can lead to a vigorous T response for two reasons. First, with a paucity of the hydrophobic anchor residues identified as being important in the binding of peptides to MHC molecules, it probably lacks MHC binding motiffs. Second, the preponderance of prolines in this peptide is certain to introduce significant kinking into the peptide backbone, and these kinks may inhibit stable binding to MHC. Third, even if MHC binding motiffs are present within the peptide, they may not be processed appropriately for MHC binding by antigen presenting cells. The topic of peptide binding to MHC molecules is reviewed concisely by L. D. Barber and P. Parham ("The essence of epitopes". 1994. Journal of Experimental Medicine. volume 180. pages 1191–1194).

The trials described in Tables 2 and 3 above are not equivalent in the sense that the immunization protocols are not identical. Still it is instructive to compare the data between them for Balb/C ByJ and SJL mice. ELISA results from Balb/c immunized with and without Ribi adjuvant are presented in FIGS. 8 and 9, respectively. ELISA results from SJL mice immunized with and without Ribi adjuvant are presented in FIGS. 10 and 11, respectively.

Immune responses in each mouse strain appear from the ELISA data to be somewhat stronger following immunization with Ribi adjuvant. Yet the responses appear qualitatively similar. Interestingly, in each strain immunizations without Ribi adjuvant appear to induce stronger immune responses against LTB than immunizations with Ribi adjuvant. In Balb/c mice the antibody response against LTB appears to be significantly stronger than the response against hCG. On the other hand, in SJL mice this is clearly not the case since their response to hCG is on a par with that to LTB. The fact that the immunization protocols with and without Ribi adjuvant were not identical limits the extent to which conclusions can be drawn regarding the quantitative effects of adjuvant on the immune response. However, it is clear that there is an antibody response to hCG epitopes in every Balb/c ByJ and SJL/J animal tested. Furthermore, it's also clear that these specific antibodies are induced by the LTB-CTP fusion protein and that additional adjuvant beyond that supplied by a microbial gene product is not necessary for a high titer immune response.

It should be noted that in the mouse trial using Ribi adjuvant, a third immunization was performed with adjuvant plus LTB-CTP fusion proteion. In a prior ELISA experiment, results following the third immunization using Ribi adjuvant were very similar to those following the second immunization. However, these results are not presented here since in this type of analysis there are slight variations in results from assay to assay. Thus it's important when comparing samples to use data which has all come from the same assay. All of the data presented in Tables 1, 2, and 3, as well as FIGS. 8, 9, 10, and 11 were collected at the same time in the same assay.

7 EXAMPLE

7.1 Procedures for Recombinant Plasmid Preparation 7.1.1 Bacteria and plasmids *E. coli* DH5-alpha is a restriction negative strain used for transformation. The pBR322-beta-hCG plasmid, grown in and purified from *E. coli* strain K-12 was used as a template for the polymerase chain reaction. The pUC18 plasmid with its polylinker cloning site downstream of the lac promoter was used as a vector to express LTB and the LTB-CTP fusion protein. pUC18 is 2.68 kb in length and is similar to pUC19, but the polylinker sequence is reversed (Yanisch-Perron, C., et al. "Improved M13 phage cloning vectors and host strains: nucleotide sequences of the M13mp18 and pUC19 vectors". 1985. Gene. volume 33. pages 103–119).

7.1.2 Manipulation of Gene Products

Oligonucleotides were constructed using the Applied Biosystems 295 DNA/RNA Synthesizer using ABI reagents and the standard protocol. PCR amplification was performed with one microgram of plasmid DNA and primer for ten cycles of one minute at 94° C., one minute at 55° C. and 30 seconds at 72° C. Primers were present at a concentration of 1 micromolar and deoxynucleotides at 200 micromolar. The PCR buffer contained 50 millimolar KCl, 10 millimolar Tris-HCl (pH 8.3 at room temperature), 1.5 millimolar MgCl(2), and 0.01% gelatin.

Plasmid DNA was isolated for preparative purposes and for screening recombinants by alkaline-lysis (T. Maniatis, et al. "Molecular Cloning", second edition. 1989. Cold Spring Harbor Press, Cold Spring Harbor). Restriction endonucleases and reagents were obtained from New England Biolabs, Inc.; digests were all performed at 37 degrees Centigrade for one to four hours.

Analytical agarose gel electrophoresis was performed on 1–1.4% horizontal slab gels in 0.04M Tris, 0.2M sodium acetate, and 0.002M EDTA, pH 7.8 (1X TAE). For isolation of the PCR product, a 3% Nu-Sieve agarose gel in 1X TAE was used. A 1% low-melting point agarose gel in 1X TAE was used for isolation of other DNA fragments. Bacteriophage lambda DNA fragments from HindIII digestion provided by New England Biolabs and 1 kb DNA ladder made by Gibco were used a molecular weight standards. Staining of the gel was done in 0.5 micrograms/milliliter ethidium-bromide, and the gel was viewed in long-wave UV light (260 nm).

DNA fragments were excised from gels to Eppendorf tubes and the volume brought up to 500 microliters at 0.3M sodium acetate. Tubes containing gel slices were then heated for 5 minutes at 70° C., placed in dry ice for 5 minutes, and centrifuged at 14,000 rpm in a microfuge at 4° C. for 15 minutes. Supernatant was transferred to a new tube, and 1 milliliter of 100% ethanol was added for precipitation for 15 minutes at 4 degrees centigrade. Tubes were then centrifuged for an additional 15 minutes at 14,000 rpm and the supernatant discarded. The precipitate was then rinsed with 0.5 milliliter of 70% ethanol, vacuum dried, and resuspended in 10 microliters of 10 mM Tris, 1 mM EDTA (TE), pH 8.0.

7.1.3 T4 DNA Ligation, Transformation and Recombinant Isolation

T4 DNA ligase was obtained from New England Biolabs. Reactions were performed at 15 degrees Centigrade overnight. DNA to be used for electroporation was precipitated with equal volumes of 5.0 molar ammonium acetate and ethanol for 30 minutes at room temperature then centrifuged for 15 minutes at 14,000 rpm in a microfuge, rinsed with 70% ethanol, air dried, and resuspended in 7 microliters of 10 mM Tris, 1 mM EDTA (TE) .

Electroporation of plasmid DNA was done using a Gene Pulser set at 2.5 kilovolts, 25 microFarads, and 200 Ohms. 35 microliters of electrocompetent bacteria was mixed with 3 microliters of salt-free DNA, pulsed, added to 1 milliliter of LB broth, and incubated at 37° C. shaking for 1 hour, and then plated on selective medium.

7.1.4 DNA sequencing of Recombinants

Sequencing was also performed on an Applied Biosystems, Inc. (ABI) sequencer using standard ABI kits and protocol.

7.2 Methods for Analysis of Recombinant Gene Product 7.2.1 Enzyme-Linked Immunosorbent Assays For analysis of bacterial sonicates, GM1 ELISAs were done essentially as described (A. M. Svennerholm and J. Holmgren. "Identification of *Escherichia coli* heat-labile enterotoxin by means of a ganglioside immunosorbent assay (GM1-ELISA) procedure". 1978. Current Microbiology. volume 1. pages 19–23; and A. Marcello, et al. "Efficient extracellular production of hybrid *E. coli* heat-labile enterotoxin B subunits in a marine Vibrio". 1994. FEMS Microbiology Letters. volume 117. pages 47–51). 96-well plates were coated with 300 nanograms per well of $G_{M1}$ ganglioside (Sigma; St. Louis, Mo.) in 50 microliters. Plates were then washed three times with phosphate-buffered saline, 0.05% Tween 20 (PBS-T) and blocked for one hour at room temperature or overnight at 4 degrees Centigrade with 200 microliters of PBS, 5% (weight/volume) nonfat dry milk (PBS-M). Ganglioside-coated plates were then incubated for one hour at room temperature or overnight at 4 degrees Centigrade with 100 microliters of a bacterial sonicate. Following additional washes with PBS-T, specific antisera were added to wells in triplicate and incubated for one hour at room temperature or overnight at 4 degrees Centigrade. Wells were then washed again three times with PBS-T before 100 microliters of an appropriate secondary antiserum conjugated to horseradish peroxidase (HRP) was added to all wells and incubated at room temperature for one hour. Following a final three washes with PBS-T, 100 microliters of a 1 milligram/milliliter solution of o-phenylenediaminedihydrochloride in 0.1M citrate acetate buffer (pH 4.5) was added to each well and the absorbance measured at 490 nm. Specific primary antisera at 1:200 dilution were rabbit anti-CTP (V. C. Stevens. "Use of synthetic peptides as immunogens for developing a vaccine against human chorionic gonadotropin". 1986. CIBA Foundation Symposium. volume 119. pages 200–225) and goat anti-LT (obtained from John Clements of Tulane University). Secondary antisera conjugated to horseradish peroxidase (HRP) were used at dilutions recommended by the manufacturer and included donkey anti-rabbit (Amersham; Arlington Heights, Ill.), and rabbit anti-goat (Zymed; South San Francisco, Calif.).

7.2.2 Size Exclusion Chromatography

Size exclusion chromatography was performed using a Superose 12 column on an FPLC System, both made by Pharmacia (Uppsala, Sweden). Protocols were supplied by the manufacturer. 540 micrograms of bacterial sonicate, from 16 to 120 micrograms of purified LTB-CTP fusion protein, or molecular weight size standards were loaded onto the column and eluted with 50 millimolar Tris-HCl, 50 millimolar NaCl, pH 8.0. Fraction size was 1 milliliter.

7.2.3 Sodium Dodecyl Sulfate Polyacrylamide Gel Analysis

Sodium dodecyl sulfate—polyacrylamide gel electrophoresis (SDS-PAGE) was performed at 15% gel concentration according to Maniatis, et al. ("Molecular Cloning", second edition. 1989. Cold Spring Harbor Press, Cold Spring Harbor). Proteins were denatured in preparation for electrophoresis by heating to 95 degrees Centigrade for five minutes in Laemmli lysis buffer. Molecular weight standards were made by Bio-Rad (Richmond, Calif.). The proteins were run at 150 V through the stacking gel, then at 100 V for about 5 hours. Staining was performed overnight with Coomassie brilliant blue (0.1%). Destaining was performed for 5 hours in 30% methanol, 10% acetic acid.

7.2.4 Immunoblotting

Immunoblotting was performed according to standard protocol as prescribed by Maniatis et. al. ("Molecular Cloning", second edition. 1989. Cold Spring Harbor Press, Cold Spring Harbor). A Bio-Rad Trans-Blot Electrophoretic Transfer Cell was used for transfer of proteins from gel to membrane with buffer concentrations of 25 mM Tris, 192 mM glycine, 20% methanol, pH 8.3. Nitrocellulose or Millipore Immobilon-P membranes were used, and transfer was done overnight at 30 volts and 100 milliAmps in chilled buffer.

Membrane was probed with antibody diluted in either 3% BSA in PBS or in 5% non-fat dry milk in PBS and incubated in either flat trays or sealed bags. All blocking steps occurred in 5% non-fat dry milk in PBS. Monoclonal antibody AS11 was provided by Jeffrey Lillard. Secondary antibodies were horseradish peroxidase conjugated (HRP) and included donkey anti-rabbit (Amersham; Arlington Heights, Ill.) and goat anti-mouse (Pierce; Rockford, Ill.). Detection occurred by chemiluminesence using the ECL system (Amersham) for 1 minute at room temperature. The membrane was then blotted dry with Whatman 3MM paper, covered with plastic wrap, and exposed to film for 2 minutes. Based on the strength of detected bands, the membrane was exposed to film for longer or shorter time intervals to optimize detection.

7.2.5 N-terminal sequencing

Automated Edman degradation was performed on an Applied Biosystems, Inc. (ABI) machine using standard manufacturer supplied protocols and reagents.

7.2.6 Mass spectroscopy

"Electrospray" mass spectroscopy was performed with equipment and software made by Hewlett-Packard (Palo Alto, Calif.).

7.3 Recovery of Recombinant Gene Product 7.3.1 Expression of Fusion Peptide in *E. coli*

Freshly diluted cultures of *E. coli* strain DH5-alpha harboring pRE20, the LTB-CTP expression vector, were grown for sixteen hours in 2xYT medium (Maniatis et. al. "Molecular Cloning", second edition. 1989. Cold Spring Harbor Press, Cold Spring Harbor). Plasmid selection was maintained by supplementation of culture media with ampicillin at 100 micrograms/milliliter.

7.3.2 Harvesting of Fusion Peptide

Bacteria were harvested by centrifugation for twenty minutes at 4,000 g. Following supernatant decantation, cells were resuspended in 10 mM Tris-HCl,0.9% NaCl, pH 8.5 then disrupted by sonication (Branson Sonic; Danbury, Conn.). After removal of debris by centrifugation of the sonicate for twenty minutes at 10,000 g, the fusion protein was fractionated by adding solid ammonium sulfate to 65% saturation, incubated overnight at 4 degrees Centigrade, and then centrifuged for ten minutes at 10,000 g. The precipitate was resuspended in TEAN buffer (50 mM Tris-HCl, 0.2M NaCl, 3 mM $NaN_3$, 1 mM EDTA, pH 7.5) and dialyzed thoroughly against the same buffer.

7.3.3 Affinity Chromatographic Purification of Fusion Peptide

Forty five milliliters of immobilized D-galactose (Pierce; Rockford, Ill.) was packed into a 25×130 cm column and washed with 500 milliliters of TEAN buffer. Crude toxin was added to the column in TEAN buffer, after which the column was washed with an additional 500 milliliters of TEAN. Thereafter 0.3M galactose in TEAN buffer was applied to the column to elute the LTB-CTP fusion protein. Fractions were tested for presence and purity of LTB-CTP by SDS-PAGE. Positive fractions were pooled then dialyzed exhaustively with PBS before administration to animals. Concentrations were determined by UV absorbance at 280 nanometers.

7.4 Production of anti-self Immune Response using Fusion Peptide 7.4.1 Blood Collection Prior to all blood collection and immunizations, animals were anesthetized to minimize their discomfort. Rabbits were anesthetized by subcutaneous injection of 0.062 milliliters/kilogram Innovar-Vet (fentanyl) according to manufacturer's directions. Bleeding was then from the central artery of the ear pinna using a 21 gauge needle, after which animals were given naloxone subcutaneously in order to counteract effects of the narcotic fentanyl. Mice were anesthetized by inhalation of Metafane (methoxyflurane) and bled retroorbitally using a Pasteur pipet.

Blood was collected from each animal prior to their being immunized. All of these control sera were subsequently shown to lack antibody reactivity for either LTB or hCG at a 1:100 dilution. In addition, blood was collected approximately ten days following the second or third immunizations of each animal.

Following collection, blood was incubated for one hour at room temperature to allow clotting to occur. The clot was then dislodged from the wall of the collection tube and the vessel incubated overnight at 4 degrees Centigrade to allow for clot retraction. Finally, clots were removed by centrifugation and sera stored at −20 degrees Centigrade until ELISA analysis.

7.4.2 Immunizations

Two New Zealand White rabbits (5–6 pounds each) were immunized with LTB-CTP fusion protein plus Ribi adjuvant R-730 (Ribi Immunochem Research; Hamilton, Mont.). Fusion protein was mixed with adjuvant according to manufacturer's instructions. Each rabbit was given three immunizations at roughly 30 day intervals. The first immunization consisted of adjuvant plus 650 micrograms of fusion protein (162 micrograms equivalent of CTP) administered intradermally, intramuscularly, and intraperitoneally. Additional immunizations consisted of adjuvant plus 450 micrograms of fusion protein (112 micrograms equivalent of CTP).

Mice were immunized in groups of five. Strains used were Balb/c ByJ, C57BL/6, and SJL/J. All mice were females, between eight and twelve weeks of age at time of first injection. Two mouse immunization trials were conducted. In the first, Balb/c ByJ and SJL/J mice were immunized on two occasions with Ribi R-700 adjuvant plus approximately 200 micrograms of LTB-CTP fusion protein (50 micrograms equivalent of CTP). Antigen administrations were by subcutaneous and intraperitoneal injection at roughly four week intervals.

In a second trial, Balb/c ByJ, C57BL/6, and SJL/J mice were immunized on three occasions with approximately 300 micrograms of LTB-CTP fusion protein (75 micrograms equivalent of CTP) in PBS without additional adjuvant. Antigen administrations were by subcutaneous injections at roughly four week intervals.

7.4.3 Enzyme-Linked Immunosorbent Assays

For analysis of antibodies from immunized animals to LTB, ELISAS were done essentially as described in Section 7.2.1, with the following modifications. Ganglioside-coated plates were incubated overnight at 4 degrees Centigrade with 50 microliters of a purified 20 micrograms/milliliter solution of LTB protein and washed again. Test or control antisera diluted in PBS-M were added to wells in triplicate and incubated overnight at 4 degrees Centigrade. Wells were then washed again three times with PBS-T. Then 100 microliters of an appropriate secondary antiserum conjugated to horseradish peroxidase (HRP) was added to all wells and incubated at room temperature for one hour. Secondary antisera were donkey anti-rabbit (Amersham; Arlington Heights, Ill.) and goat anti-mouse (Pierce; Rockford, Ill.), each diluted according to manufacturer's instructions. Following a final three washes with PBS-T, 100 microliters of a 1 milligram/milliliter solution of o-phenylenediaminedihydrochloride in 0.1M citrate acetate buffer (pH 4.5) was added to each well and the absorbance measured at 490 nm. Control antisera were rabbit anti-CTP (V. C. Stevens. "Use of synthetic peptides as immunogens for developing a vaccine against human chorionic gonadotropin". 1986. CIBA Foundation Symposium. volume 119. pages 200–225) and goat anti-LT (the gift of John Clements, Tulane University).

For hCG ELISAs, microtiter trays were coated with 50 microliters per well of purified hCG (Intergen; Purchase, N.Y.) at 4 micrograms/milliliter in PBS for 24 hours at 4° Centigrade. After 3 washes with PBS-T, sera diluted in PBS-M were added to wells in triplicate and incubated for one hour at room temperature. Following three washes with PBS-T, secondary antisera linked to HRP and diluted in PBS-M were added to wells and incubated for one hour at room temperature. After a final three washes, 100 microliters of a 1 mg/milliliter solution of o-phenylenediamine in 0.1M citrate-acetate buffer (pH 4.5) was added to each well, and the absorbance at 490 nm was read on a microplate reader (Molecular Devices; Menlo Park, Calif.).

Titers were defined as the last dilution at which the mean of absorbance values for a given antiserum remained significantly above the mean of background values when primary (test) antiserum was omitted. All ELISA results presented here were obtained in the same analysis of sera and are thus internally consistent. In addition, each serum was tested at least twice, and results of multiple ELISA analyses are essentially identical.

8 CONCLUSION, RAMIFICATIONS, AND SCOPE

In summary, this invention relates to the field of novel vaccine compositions which break immunological self-tolerance and processes for producing such compositions. Self-tolerance is broken via immunization with a recombinant gene product which combines a self protein product with a microbial gene product which includes both helper T cell epitopes and adjuvant activity. Advantages of this strategy to break down self-tolerance include greater consistency of immunogen preparation, lower cost of manufacture, and greater ease of administration.

As an example, a fusion protein of LTB linked to the carboxyl terminal peptide (CTP) of hCG has been engineered. This protein is stably expressed and renders the CTP immunogenic in mice without additional adjuvant. Such a formulation may be useful in vaccination strategies against hCG. Thus the reader will see that the invention described provides a versatile, economic, and effective system to break self-tolerance in humans and other higher vertebrates.

While my above description contains many specifications, these should not be construed as limitations on the scope of the invention but rather as an exemplification of one preferred embodiment thereof. Many other variations are possible. Accordingly, the scope of the invention should be determined not by the embodiment(s) illustrated, but by the appended claims and their legal equivalents.

I claim:

1. A method of breaking self-tolerance against self protein in a mammal, which comprises administering to the mammal a self-tolerance breaking effective amount of a fusion protein for eliciting an immune response, said fusion protein comprising pentamers of *Escherichia coli* labile toxin subunit B and human chorionic gonadotropin.

2. The method of claim 1, wherein the fusion protein is administered via the mucosal membrane.

3. A method of inducing antibody against self protein in a mammal, which comprises administering to the mammal an antibody inducing effective amount of a fusion protein for eliciting an immune response, wherein the recombinant gene product comprises pentamers of *Escherichia coli* labile toxin subunit B and human chorionic gonadotropin.

4. The method of claim 3, wherein the fusion protein is administered via the mucosal membrane.

5. An isolated fusion protein comprising pentamers of *Escherichia coli* labile toxin subunit B and human chorionic gonadotropin.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:

( A ) LENGTH: 45 base pairs

-continued ( B ) TYPE: nucleic acid
( C ) STRANDEDNESS: single
( D ) TOPOLOGY: linear ( x i ) SEQUENCE DESCRIPTION: SEQ ID NO: 1:

```
GTCCCAAGGA CCACCTGCAG ACCAGTGATG ACCCCCGCTT CCAGG                    45
```

( 2 ) INFORMATION FOR SEQ ID NO: 2:

( i ) SEQUENCE CHARACTERISTICS:
( A ) LENGTH:33 base pairs
( B ) TYPE: nucleic acid
( C ) STRANDEDNESS: single
( D ) TOPOLOGY: linear ( x i ) SEQUENCE DESCRIPTION: SEQ ID NO: 2:

```
CGGATTGAGA AGCCTTTATT GTTGGAGGAT CGG                                 33
```

( 2 ) INFORMATION FOR SEQ ID NO: 3:

( i ) SEQUENCE CHARACTERISTICS:
( A ) LENGTH: 532 base pairs
( B ) TYPE: nucleic acid
( C ) STRANDEDNESS: single
( D ) TOPOLOGY: linear ( x i ) SEQUENCE DESCRIPTION: SEQ ID NO: 3:

```
GAATTCGGAA TGAATT ATG AAT AAA GTA AAA TGT                                    34
                  Met Asn Lys Val Lys Cys
                      -20             -16

TAT GTT TTA TTT ACG GCG TTA CTA TCC TCT CTA TGT GCA TAC GGA                  79
Phe Val Leu Phe Thr Ala Leu Leu Ser Ser Leu Cys Ala Tyr Gly
-15                 -10                 -5                  -1

GCT CCC CAG TCT ATT ACA GAA CTA TGT TCG GAA TAT CGC AAC ACA                 124
Ala Pro Gln Ser Ile Thr Glu Leu Cys Ser Glu Tyr Arg Asn Thr
  1               5                  10                  15

CAA ATA TAT ACG ATA AAT GAC AAG ATA CTA TCA TAT ACG GAA TCG                 169
Gln Ile Tyr Thr Ile Asn Asp Lys Ile Leu Ser Tyr Thr Glu Ser
                 20                  25                  30

ATG GCA GGC AAA AGA GAA ATG GTT ATC ATT ACA TTT AAG AGC GGC                 214
Met Ala Gly Lys Arg Glu Met Val Ile Ile Thr Phe Lys Ser Gly
                 35                  40                  45

GCA ACA TTT CAG GTC GAA GTC CCG GGC AGT CAA CAT ATA GAC TCC                 259
Ala Thr Phe Gln Val Glu Val Pro Gly Ser Gln His Ile Asp Ser
                 50                  55                  60

CAA AAA AAA GCC ATT GAA AGG ATG AAG GAC ACA TTA AGA ATC ACA                 304
Gln Lys Lys Ala Ile Glu Arg Met Lys Asp Thr Leu Arg Ile Thr
                 65                  70                  75

TAT CTG ACC GAG ACC AAA ATT GAT AAA TTA TGT GTA TGG AAT AAT                 349
Tyr Leu Thr Glu Thr Lys Ile Asp Lys Leu Cys Val Trp Asn Asn
                 80                  85                  90

AAA ACC CCC AAT TCA ATT GCG GCA ATC AGT ATG GAA AAC CAT GAT                 394
Lys Thr Pro Asn Ser Ile Ala Ala Ile Ser Met Glu Asn His Asp
                 95                 100                 105

CCC CGG GTA CCC GGG CTG CAG ACC AGT GAT GAC CCC CGC TTC CAG                 439
Pro Arg Val Pro Gly Leu Gln Thr Ser Asp Asp Pro Arg Phe Gln
                110                 115                 120

GAC TCC TCT TCC TCA AAG GCC CCT CCC CCG AGC CTT CCA AGT CCA                 484
Asp Ser Ser Ser Ser Lys Ala Pro Pro Pro Ser Leu Pro Ser Pro
                125                 130                 135

TCC CGA CTC CCG GGG CCC TCG GAC ACC CCG ATC CTC CCA CAA TAAAGC              532
Ser Arg Leu Pro Gly Pro Ser Asp Thr Pro Ile Leu Pro Gln
                140                 145             149
```